United States Patent
Chitte et al.

(12) 
(10) Patent No.: US 6,638,503 B2
(45) Date of Patent: Oct. 28, 2003

(54) STREPTOMYCES MEGASPORUS SD5, PROCESS FOR THE ISOLATION THEREOF, NOVEL FIBRINOLYTIC ENZYME PREPARED THEREFROM, PROCESS FOR THE PRODUCTION OF SAID ENZYME AND METHOD OF TREATMENT OF THROMBOLYTIC DISORDERS USING SAID ENZYME

(75) Inventors: Ratnakar Ravindra Chitte, Pune (IN); Sabita Dey, Pune (IN)

(73) Assignee: Maharashtra Association for the Cultivation of Science, Pune (IN)

( * ) Notice: Subject to any disclaimer, the term of this patent is extended or adjusted under 35 U.S.C. 154(b) by 0 days.

(21) Appl. No.: 09/997,196

(22) Filed: Nov. 28, 2001

(65) Prior Publication Data

US 2003/0170221 A1 Sep. 11, 2003

(51) Int. Cl.[7] .................. A61K 38/48; C12P 21/04; C12N 9/70; C12N 9/52

(52) U.S. Cl. ................. 424/94.64; 435/71.1; 435/71.2; 435/71.3; 435/212; 435/213; 435/216; 435/220; 435/252.35; 435/886; 424/94.63; 930/240

(58) Field of Search ............................ 435/252.35, 212, 435/213, 216, 220, 886, 71.1, 71.2, 71.3; 930/240; 424/94.64, 94.63

(56) References Cited

U.S. PATENT DOCUMENTS 5,795,759 A * 8/1998 Rozazza et al. ............. 435/219
6,159,722 A * 12/2000 Bode et al. ................. 435/219

* cited by examiner

Primary Examiner—Herbert J. Lilling
(74) Attorney, Agent, or Firm—Ladas & Parry

(57) ABSTRACT

The present invention relates to a novel microorganism *Streptomyces megasporus* SD5. The present invention also relates to a process for the isolation of said *Streptomyces megasporus* SD5. The invention also relates to a novel fibrinolytic enzyme actinokinase extracted from said microorganism and to a process for the extraction of said enzyme. In another aspect, the invention also pertains to a method for the treatment of thrombolytic disorders using said enzyme.

36 Claims, 7 Drawing Sheets

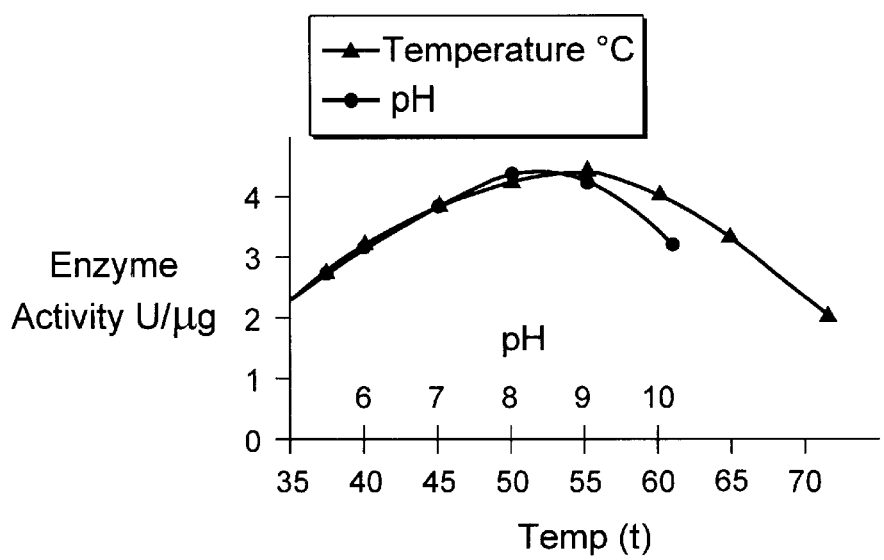
F I G. 1. Optimum temperature and pH for synthesis of thrombolytic enzyme of *S. megasporus* SD5
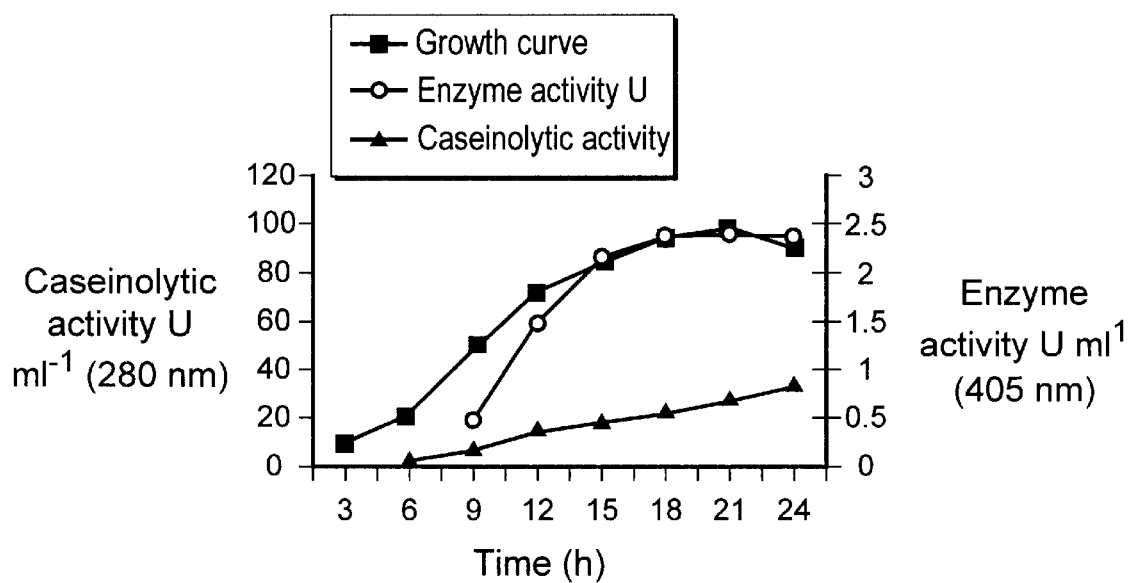
F I G. 2. Thrombolytic and caseinolytic activities with relation to growth of *S. megasporus* strain SD5

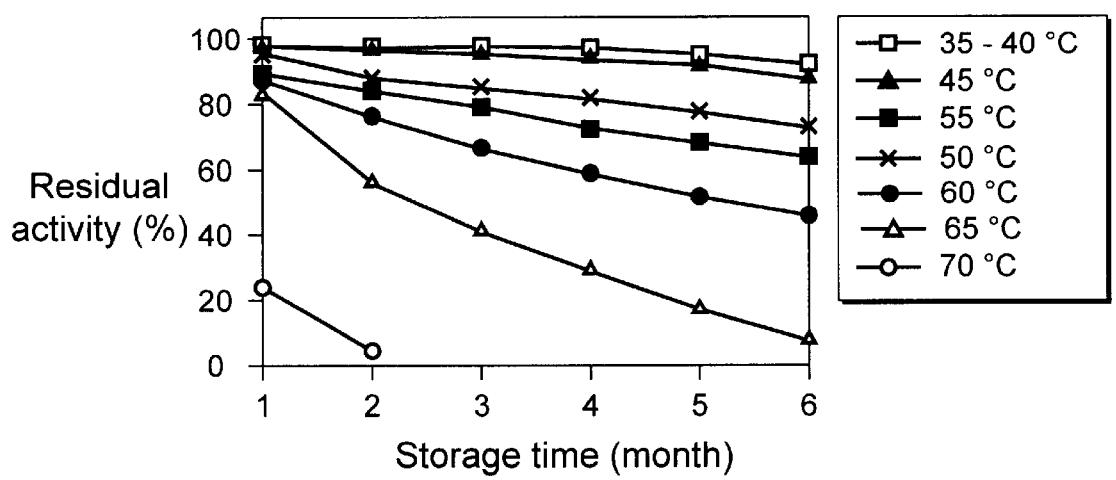
F I G. 3. Effect of storage times (1-6) on enzyme activity at different temperature.
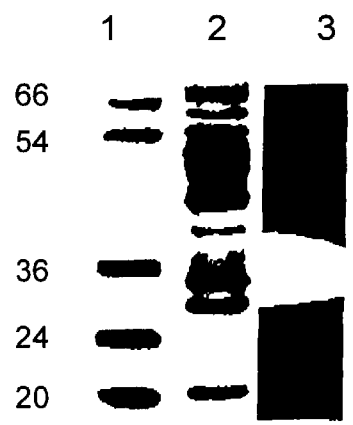
F I G. 4. Gel electrophoresis of
1. Molecular weight marker
2. Crude enzyme
3. Zymogram of thrombolytic enzyme using chromogenic substrate.

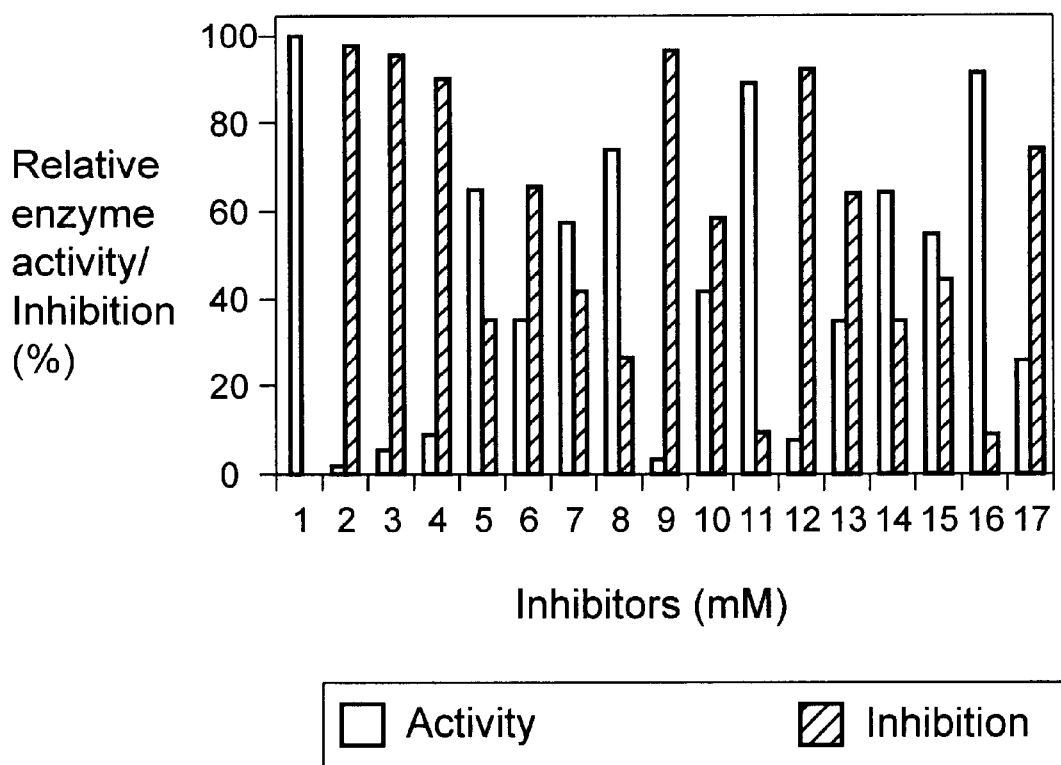
FIG. 5. Effect of inhibitors on enzyme activity
1. Control
2. Antipain
3. Bestatin
4. Chymostatin
5. E-64
6. Leupeptin
7. Pepstatin
8. Phosphoramidon
9. Pefabloc
10. EDTA
11. EDTA+ $Ca^{2+}$
12. Aprotinin
13. Trypsin inhibitor
14. β-Mercaptoethanol
15. TPCK
16. 1,10 Phenanthrolin
17. PMSF

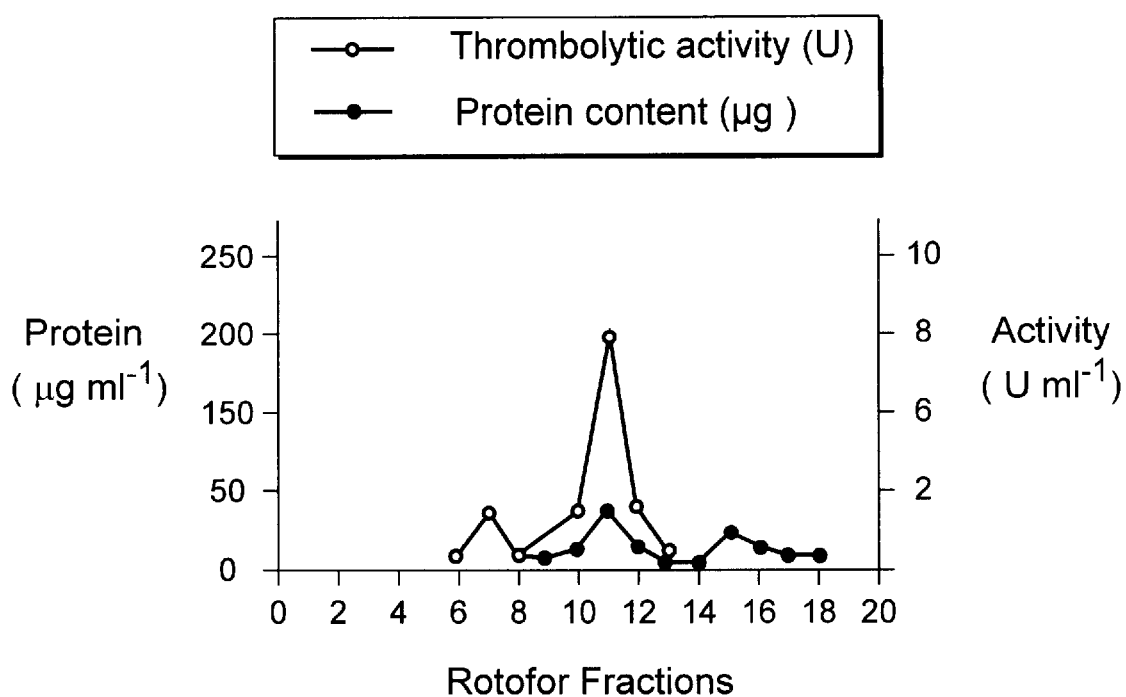
F I G. 6. Refractions of the semipurified trombolytic enzyme using Rotofor System (Bio Rad. USA)
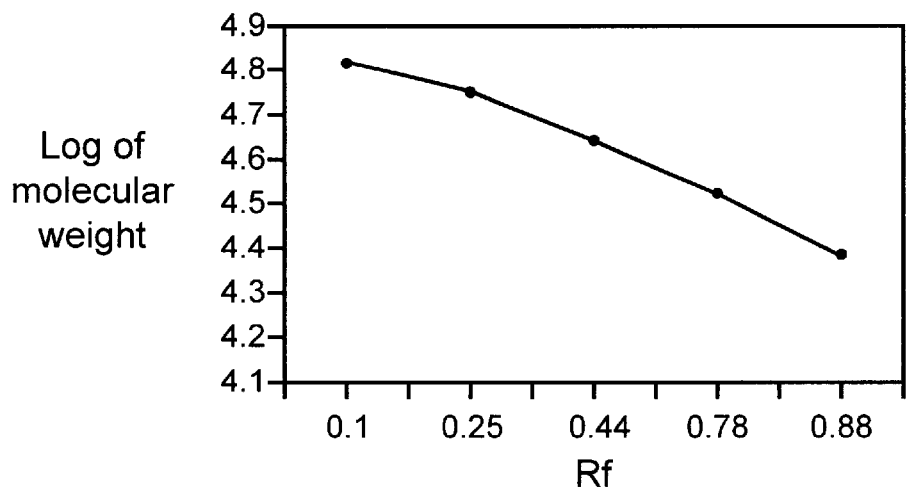
F I G. 8. Calibration curve of the enzyme along with standard protein markers (24 - 66 kDa).

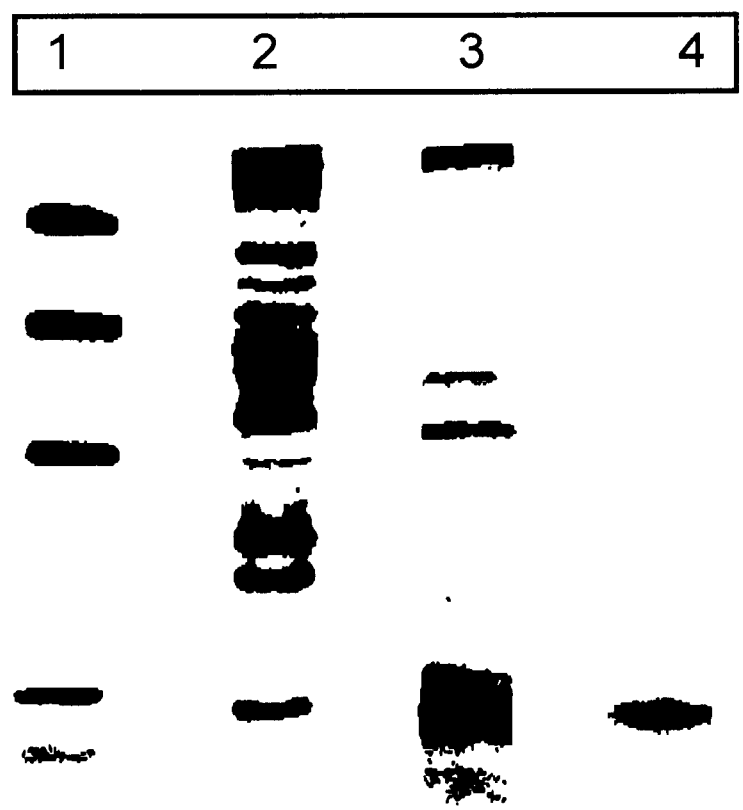
F I G. 7. SDS - PAGE of Actinokinase
Lane 1- Protein marker (24 -66 KDa).
Lane 2- Crude wild protein.
Lane 3 - Partially purified protein.
Lane 4 - Purified protein.

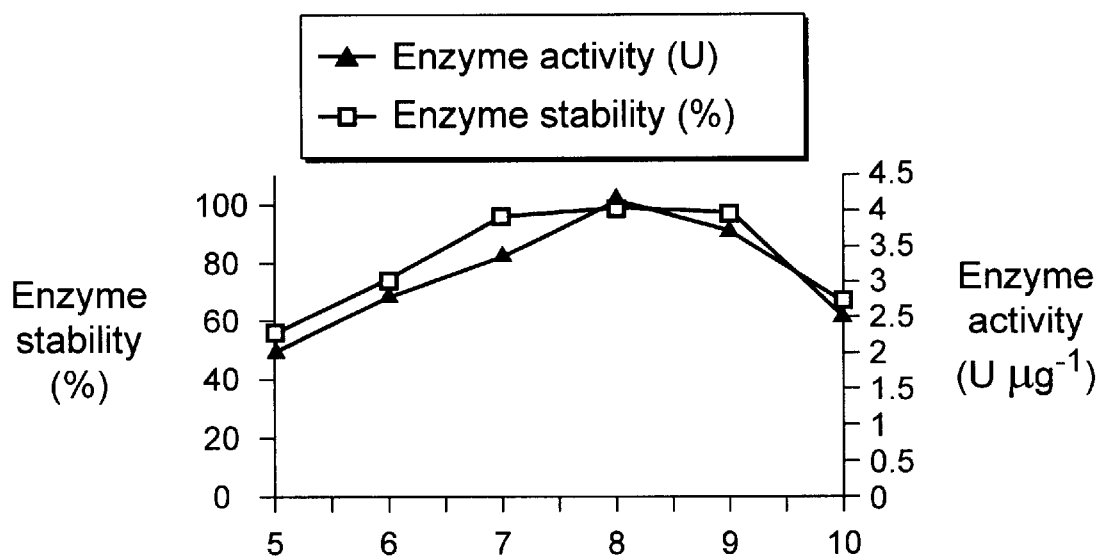
F I G. 9. Effect of different pH on the stability and activity of the thrombolytic enzyme.
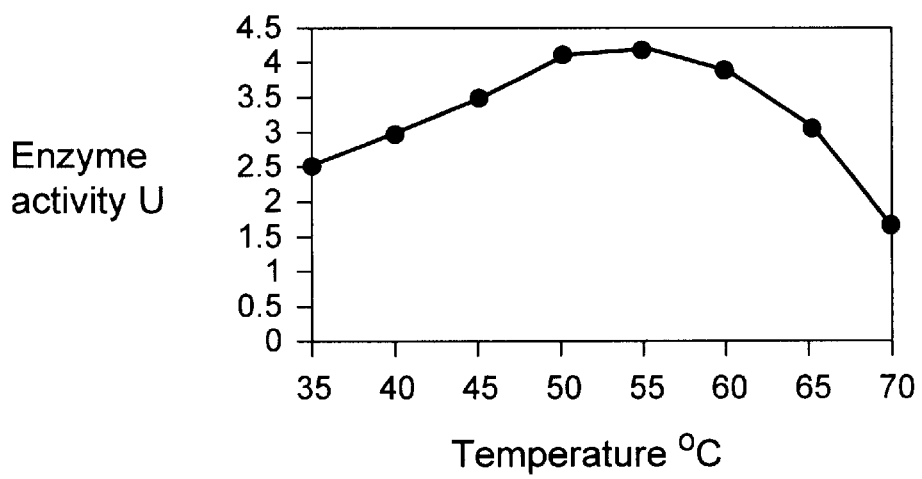
F I G. 10. Optimum temperature for the activity of the thrombolytic enzyme

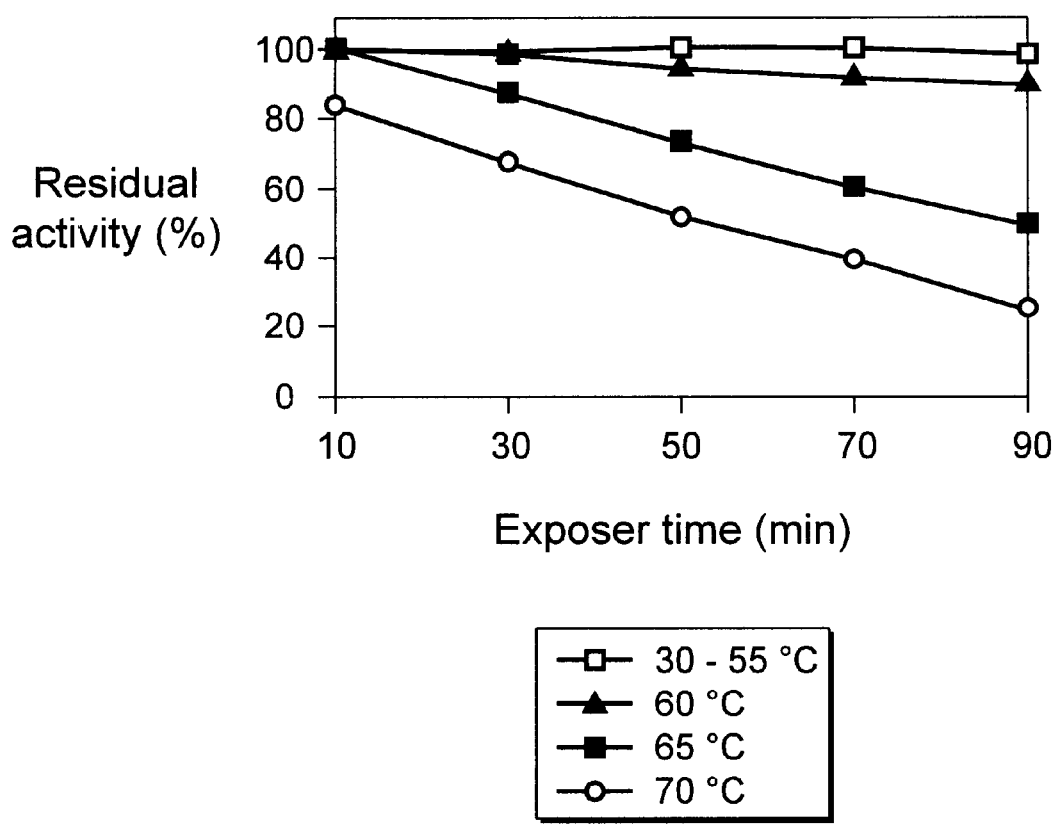
F I G. 11. Effect of temperature on the stability of the thrombolytic enzyme.

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial
<220> FEATURE:
<223> OTHER INFORMATION: This peptide was synthetically generated.

<400> SEQUENCE: 1

Pro Phe Ala Arg
1

<210> SEQ ID NO 2
<211> LENGTH: 4
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (2)..(2)
<223> OTHER INFORMATION: /product = D-phenylalanine/label = D-Phe

<400> SEQUENCE: 2

Met Xaa Gly Arg
1

<210> SEQ ID NO 3
<211> LENGTH: 16
<212> TYPE: PRT
<213> ORGANISM: Artificial
<220> FEATURE:
<223> OTHER INFORMATION: This peptide was synthetically generated.

<400> SEQUENCE: 3

Asp Glu Asn Gln Ser Thr Gly Ala Tyr Val Pro Pro Tyr Phe Ile Leu
1               5                   10                  15
```

STREPTOMYCES MEGASPORUS SD5, PROCESS FOR THE ISOLATION THEREOF, NOVEL FIBRINOLYTIC ENZYME PREPARED THEREFROM, PROCESS FOR THE PRODUCTION OF SAID ENZYME AND METHOD OF TREATMENT OF THROMBOLYTIC DISORDERS USING SAID ENZYME

FIELD OF THE INVENTION

The present invention relates to a novel microorganism *Streptomyces megasporus* SD5. The present invention also relates to a process for the isolation of said *Streptomyces megasporus* SD5. The invention also relates to a novel fibrinolytic enzyme actinokinase extracted from said microorganism and to a process for the extraction of said enzyme. In another aspect, the invention also pertains to a method for the treatment of thrombolytic disorders using said enzyme.

BACKGROUND OF THE INVENTION

Thrombosis of critical blood vessels results in the loss of blood flow to vital organs thereby resulting in mortality. In vivo formation of thrombus is a pathological consequence of interactions between the hemostatic mechanism of blood and the components of injured vessels. [Collen, On the future of thrombolytic therapy in acute myocardial infarction, Haber E., and Braunwald E., editors Thrombolysis: Basic contribution and clinical progress, 1991, St. Louis, Mo., Mosby, p. 131]. In recent years, the treatment of thrombosis has focused on pharmacological dissolution of the thrombus. Thrombolytic therapy has now become the established procedure for recanalizing the occluded myocardial blood vessels and thereby reducing mortality. Thrombolytic agents are plasminogen activators that convert plasminogen, the inactive proenzyme of the fibrinolytic system of blood to the active proteolytic enzyme, plasmin. Several plasminogen activators are disclosed in the prior art such as streptokinase [Castellino, et al, 1993, *Met.in.Enz*, 222, 244–255]; staphylokinase [Trien, et al, 1993, *Met.in.Enz*, 223, 156–167]; urokinase [Barlow, 1993, *Met.in.Enz*, 222, 239–243] and tissue plasminogen activators [Lijnen H. R. and Collen D., 1993, *Met.in.Enz*, 223, 197–205], both in native and recombinant forms.

The search for therapeutic agents useful in the treatment of thrombosis has focused on fibrinolytic enzymes. In the search for new enzymes, attention is being given to living sources such as bacteria in view of the potential for greater efficacy [Kim H. K., Kim, G. T., Kim, D. K., Won, A. C. Park, S. H., Jeong, Y. K. & Kong, I. S. 1997. Purification and characterization of a novel fibrinolytic enzyme from Bacillus sp. KA 38 originated from fermented fish. *J. Ferment. Bioengineering* 84 (4), 307–312; Wang, J., Wang, M. and Wang Y 1999. Purification and characterization of a novel fibrinolytic enzyme from Streptomyces sp. *Clin. J. Biotech.* 15 (2) 83–89]. However, these enzymes are very expensive [Thomson, P. L., Tonkin, A. M., Aylward, P & White, H. 1993, Thrombolysis '93 Overview and conclusions. *Australian New Zealand Journal of Medicine* 23: 774–777] and occasionally show haemorrhagic side effects [Collen, D., Lijnen, H. R. & Stassen, J. N. 1993. Combination of animal models and biotechnology in the development of new thrombolytic agent, *Fibrinolysis*, 7, 36–43]. As a result it is necessary to develop new fibrinolytic enzymes that are less expensive and effective without any adverse effects.

Of the enzymes known in the art, streptokinase has predominantly been used for coronary superfussion. However, streptokinase is expensive and the origin is a pathogen. Another disadvantage in the use of streptokinase as a thromobolytic agent is that the failure rate is reportedly as high as 25%. As has been explained, known thrombolytic agents have limited efficacy and potentially life threatening side effects. Other disadvantages of known agents include requirement of large therapeutic doses, limited fibrin specificity, short half life, re-occlusion and bleeding complications.

The limitations of known thrombolytic agents can also be explained on the basis of the heterogeneity of coronary arterial thrombus, which consists of both etythrocyte and plate rich zones and the knowledge of the mechanism of fibrin dissolution and platelet de-aggregation. Prior art focuses on dissolution of whole blood clot. For example, streptolkinase and urokinase do not show any affinity for fibrin and activate circulating and fibrin bound plasminogen indiscriminately. As a result, initially formed plasmin is neutralized by $\alpha_0$-antiplasmin resulting in reduction or no action on thrombolysis, The potential of pharmacological dispersion of platelet clumps and platelet rich thrombus has not been fully explored as yet. Also, attention has not been given to complementary treatment of both the whole blood clot and the platelet clumps and platelet rich thrombus.

In view of the importance of fibrinolytic enzymes in the treatment of thrombosis in human beings, microbial sources including Streptomyces are being investigated to obtain compounds that could activate any one site in the complex and diverse fibrinolytic pathway. Interest in the search of novel thermophilic Streptomyces as producers of bioactive but non-antibiotic metabolites has increased because of thermophilic Streptomyces strains, associated with the tectonically active zones, are considered a unique and important genetic resource due to the intrinsic stability of their bioactive molecules which are extremely useful for large scale production under harsh conditions, in terms of pH and temperature.

OBJECTS OF THE INVENTION

The main object of the present invention is to develop novel thrombolytic enzymes from natural microbial sources, which are inexpensive and show increased efficacy.

It is another object of the invention is to obtain new strains of microbial organisms that could provide compounds for use as inexpensive and efficacious thrombolytic agents.

It is a further object of the invention to provide a process for the growth of new strains of microbial organisms, which could provide a source for novel compounds for use as inexpensive and efficacious thrombolytic agents.

It is another object of the invention to provide a process for the extraction of novel enzymes from isolated Streptomyces organisms, which are useful as thrombolytic agents by dispersion of platelet clumps and platelet rich thrombus.

It is another object of the invention to provide a method of treatment of thrombosis using a novel fibrinolytic enzyme obtained from a new strain of Streptomyces bacteria, which has greater efficacy as compared to the substances employed in the art.

SUMMARY OF THE INVENTION

Recent interest in biotechnology and biodiversity has prompted the search of novel thermophilic Streptomyces, producers of bioactive but nonantibiotic metabolites. Thermophilic Streptomyces strains associated with tectonically active zones are considered unique and important genetic resource due to the intrinsic stability of their bioactive molecules which are extremely useful for large scale production under harsh conditions, in terms of pH and temperature. Tectonically active zones prevail along the Western coast of Maharashtra, India. There are 60 thermal springs with a temperature range of 40° C.–90° C. in this region. Another unique site is the Lonar lake basin, a meteoritic crater, situated on the Deccan plateau. These ecosystems were selected for isolation sites as these are tectonically active, confined but microbiologically untouched area and their physicochemical properties are relatively constant. The present invention concerns a novel strain of Streptomyces (named *Streptomyces megasporus* SD5 by the applicants) isolated from such thermal springs.

Accordingly the present invention relates to a novel strain of Streptomyces named *Streptomyces megasporus* SD5 and variants and mutants thereof.

In one embodiment of the invention, *Streptomyces megasporus* SD5 comprises elongate colourless branched substrate mycelia and short aerial mycelia.

In another embodiment of the invention, the microorganism *Streptomyces megasporus* SD5 hydrolyses casein and starch and does not liquefy gelatine in different media, form $H_2S$ or reduce nitrate.

In another embodiment of the invention, the microorganism *Streptomyces megasporus* SD5 does not produce melanoid pigment on tyrosine sugar, peptone-yeast extract, iron agar and tryptone yeast extract broth.

In another embodiment of the invention, the microorganism *Streptomyces megasporus* SD5 has the following carbon assimilation pattern in Pridham-Gottileb medium:

Positive: casein, starch, glucose and fibrin

Weak: cellulose and gelatine

Negative: tributyrin, pullulan, xylan and cyclodextrin

In another embodiment of the invention, the microorganism *Streptomyces megasporus* SD5 is inhibited by thiostrepton, and lincomycin at a concentration of 50 μg $ml^{-1}$, tolerates NaCl concentration up to 1% and has a pH tolerance of from 6.0 to 9. 0.

In another embodiment of the invention, the microorganism *Streptomyces megasporus* SD5 has the profile given below in Table I.

TABLE 1

Profile of the thermophilic isolates

| Characters | Property of the thermophilic isolates |
| --- | --- |
| Substrate mycelia | Present, nonfragmented |
| Aerial mycelia | Present, short, septed |
| Spores in chains | Short chains and clusters |
| Spore surface warty | Ridges in mature spores |
| Mole % G + C | 69–70 |
| Cell wall chemo type | Type 1 (LL-DAP and Glycine) |
| Whole cell sugar pattern | No diagnostic sugars |
| 4 Mu linked enzyme substrates | Positive with phosphatases and Stearases |
| Fatty acid profile | Matching 82% with Streptomyces |
| 16 S r RNA | 95% matching with Streptomyces |

The present invention also relates to a process for the isolation of the microorganism *Streptomyces megasporus* SD5 from hot water sources and springs using a nutrient medium containing carbon and nitrogen sources in a definite ratio and inorganic nutrient salts.

In one embodiment of the invention, the isolation of the microorganism *Streptomyces megasporus* SD5 is done using a solidifying agent in combination with the nutrient medium.

In one embodiment of the invention, the carbon sources are selected from the group consisting of glucose, starch, sucrose and agricultural wastes.

In another embodiment of the invention, the nitrogen sources are selected from the group consisting of peptone, yeast extract, beef extract, malt extract, casein hydrolysates, haemoglobin and fibrin.

In another embodiment of the invention, the solidifying agents are selected from agar and agarose.

In yet another embodiment of the invention, the inorganic salts are selected from salts of calcium, sodium, potassium and magnesium.

In another embodiment of the invention, the nutrient medium comprises glucose in an amount of 0.2 to 1 g, yeast extract in an amount of 0.1 to 0.6 g, glycerol in an amount of 0.2 to 0.5 g, NaCl in an amount of 0.1 to 0.6 g and Agar as the solidifying agent.

In a further embodiment of the invention, the nutrient medium comprises glucose in an amount of 0.5 g, yeast extract in an amount of 0.5 g, glycerol in an amount of 0.5 g, NaCl in an amount of 0.5 g and Agar in an amount of 2 g as the solidifying agent.

In another embodiment of the invention, the nutrient medium comprises glucose in an amount of 1.0 g, L-asparagine in an amount of 0.5 g, yeast extract 0.5 g, peptone in an amount of 0.5 g and agar as the solidifying agent.

In another embodiment of the invention, the nutrient medium comprises (% w/v) glucose 1, yeast extract 0.5, peptone 0.5, NaCl 0.5 and $CaCl_2$ 0.2 with the pH being 8.0.

In a further embodiment of the invention, the nutrient medium comprises starch in an amount of 2.0 g, casein in an amount of 1 g and NaCl in an amount of 0.5 g.

In another embodiment of the invention, the microorganism *Streptomyces megasporus* SD5 has the following profile as given in Table I below:

TABLE 1

Profile of the thermophilic isolates

| Characters | Property of the thermophilic isolates |
| --- | --- |
| Substrate mycelia | Present, nonfragmented |
| Aerial mycelia | Present, short, septed |
| Spores in chains | Short chains and clusters |
| Spore surface warty | Ridges in mature spores |
| Mole % G + C | 69–70 |
| Cell wall chemo type | Type 1 (LL-DAP and Glycine) |
| Whole cell sugar pattern | No diagnostic sugars |
| 4 Mu linked enzyme substrates | Positive with phosphatases and Stearases |
| Fatty acid profile | Matching 82% with Streptomyces |
| 16 S r RNA | 95% matching with Streptomyces |

In another embodiment of the invention, the microorganism *Streptomyces megasporus* SD5 is mutated using conventional mutagens selected from the group consisting of N-methyl-N'-nitro-N-nitrosoguanidine, ethyl methyl sulfonate and exposure to UV radiation.

The present invention also relates to a novel enzyme named actinokinase extracted from microorganism *Streptomyces megasporus* SD5, which is useful as a thrombolytic agent.

The present invention also relates to a process for the preparation of enzyme actinokinase which comprises cultivating the microorganism *Streptomyces megasporus* SD5 or a variant or mutant thereof under aerobic conditions at a temperature in the range of 45° C. to 65° C. in an alkaline aqueous nutrient medium and recovering the enzyme.

In one embodiment of the invention, the nutrient medium comprises of carbon sources, nitrogen sources, mineral salts and trace elements and is at a pH of 7.5 to 9.0.

In another embodiment of the invention, the carbon source is selected from the group consisting of glucose, soluble starch and raw starch.

In another embodiment of the invention, the nitrogen source is selected from the group consisting of yeast extract, peptone, tryptone, casein and casein hydrolysate.

In a further embodiment of the invention, the inorganic salts used are selected from the group consisting of chlorides of calcium, sodium, potassium and magnesium.

In another embodiment of the invention, the trace elements are selected from the group consisting of iron, manganese, copper, zinc, borate and molybdenum.

In another embodiment of the invention, the temperature is maintained in the range of 50° C.–55° C. and the cultivation is carried out by fermentation, preferably submerged fermentation.

In another embodiment of the invention, an anti-foam agent, preferably soybean oil is added to the nutrient medium during fermentation.

In yet another embodiment of the invention, the enzyme is concentrated with ammonium sulphate and then separated from other proteins.

In a further embodiment of the invention, the concentrated enzyme is separated by gel filtration, ion exchange chromatography and isoelectric focusing in the presence of a buffer having a pH in the range of 3–10.

BRIEF DESCRIPTION OF THE ACCOMPANYING DRAWINGS

FIG. 1 shows the effect of temperature and pH on the synthesis of the fibrinolytic enzyme by S. megasporus SD5.

FIG. 2 shows the fibrinolytic and caseinolytic activities with relation to growth of S. megasporus SD5. Growth was measured in terms of protein determined using Folin ciocalteau method measured at 750 nm (data not shown in the graph).

FIG. 3 shows the effect of storage time at different temperatures on the residual activity of the fibrinolytic enzyme produced by S. megasporus SD5.

FIG. 4 shows the gel electrophoresis of fibrinolytic enzyme produced by S. megasporus SD5 where Lane 1 are Molecular weight markers, Lane 2 is crude enzyme, Lane 3 is a Zymogram showing fibrinolytic enzyme using fibrin plate.

FIG. 5 shows the effects of inhibitors on the activity of the fibrinolytic enzyme produced by S. megasporus SD5. 1.Control, 2—Antipain—3, Bestatin,—4, Chymostatin,—5. E-64, 6—Leupeptin, 7—Pepstatin, 8 Phosphoramidon, 9—pefabloc, 10—EDTA, 11—EDTA+$Ca^{++}$, 12—Aprotinin, 13—Trypsin inhibitor, 14β—mercaptoethanol, 15—TPCK, 16—1,10 phenanthroline, 17-PMSF.

FIG. 6 shows fractions of semi purified fibrinolytic enzyme using Rotofor System.

FIG. 7 is SDS page of fibrinolytic enzyme obtained from S. megasporus SD5.

FIG. 8 is the calibration curve of the enzyme along with standard protein markers (24–66 kDa) using gel filtration.

FIG. 9 shows the effect of different pH on the stability and activity of the fibrinolytic enzyme.

FIG. 10 shows the optimum temperature for the activity of the fibrinolytic enzyme.

FIG. 11 shows the effect of temperature on the stability of the fibrinolytic enzyme.

DETAILED DESCRIPTION OF THE INVENTION

Thermophilic Streptomyces strains associated with tectonically active zones are considered unique and important genetic resource due to the intrinsic stability of their bioactive molecules, which are extremely useful for large scale production under harsh conditions, in terms of pH and temperature. Tectonically active zones prevail along the Western coast of Maharashtra, India. There are 60 thermal springs with a temperature range of 40° C.–90° C. located in this region. Another unique site is the Lonar lake basin, a meteoritic crater, situated on the Deccan plateau. These ecosystems were selected for isolation sites as these are tectonically active, confined but microbiologically untouched area and their physicochemical properties are relatively constant.

*Streptomyces megasporus* SD5 was isolated from water of hot springs collected at Unavhre in Western Maharashtra, India. Variants and mutants of the strain SD5 are obtained in known manner using known mutagens such as N-methyl-N'-nitro-N-nitrosoguanidine, ethyl methyl sulfonate or by exposure to UV radiation.

Detailed analysis shows that the microorganism isolated belongs to the order Actinomycetes, family Streptomycetes and genus Streptomyces. The strain isolated from the hot spring water is considered to be novel since it differs from known Streptomyces sp. in terms of the morphological, cultural, physiological and genetic characteristics.

Further analysis shows that the microorganism *Streptomyces megasporus* SD5 produces an extracellular proteolytic enzyme with both caseinolytic and fibrinolytic activity that is useful as a therapeutic agent in myocardial infarction, cerebral stroke and venous thromboembolism.

*Streptomyces megasporus* SD5 produces an extracellular proteolytic enzyme with caseinolytic and fibrinolytic activity under the same conditions. The production of the enzyme can be monitored and manipulated externally depending on the requirement of the pharmaceutical industry in respect of the carbon and nitrogen sources.

The concentration of the fibrinolytic enzyme (Actinokinase) produced by *Streptomyces megasporus* SD5 and its mutants and variants are given below. Biological Abstract Service (BIOSIS), STN search for patents and Medical Literature Service (MEDLINE) searches carried out on line using the search keys fibrinolytic and caseinolytic enzyme, thermophilic and Streptomyces confirm that the thermophilic *S. megasporus* strain SD5 is a new strain of prokaryote. This strain on incubation under specific conditions produces a fibrinolytic enzyme similar to urokinase (a fibrinolytic enzyme present in fetal kidney and human urine).

The enzyme is prepared by cultivating *S. megasporus* strain SD5, its variants and mutants under aerobic conditions at a temperature in the range of 45° C. to 65° C. in an alkaline aqueous nutrient medium containing carbon sources, nitrogen sources, mineral salts and if desired trace elements at a pH between 7.5 and 9.0 and recovering the enzyme from the medium.

The enzyme is produced in crude form and can be purified to produce a fibrinolytic enzyme for use as a therapeutic agent in myocardial infarction.

*Streptomyces megasporus* SD5 comprises elongate colourless branched substrate mycelia and short aerial mycelia. Spore chains are formed after separating the aerial mycelia. Mature spores are ridged and liberate from the short aerial mycelia. The optimum growth temperature range for the microorganism of the invention is between 45° C. to 65° C.

The microorganism *Streptomyces megasporus* SD5 hydrolyses casein and starch and does not liquefy gelatine in different media, form $H_2S$ or reduce nitrate. It also does not not produce melanoid pigment on tyrosine sugar, peptone—yeast extract, iron agar and tryptone yeast extract broth. The microorganism *Streptomyces megasporus* SD5 has the following carbon assimilation pattern in Pridham-Gottileb medium:

Positive: casein, starch, glucose and fibrin
Weak: cellulose and gelatine
Negative: tributyrin, pullulan, xylan and cyclodextrin

*Streptomyces megasporus* SD5 is inhibited by thiostrepton, and lincomycin at a concentration of 50 μg ml$^{-1}$, tolerates NaCl concentration up to 1% and has a pH tolerance of from 6.0 to 9.0. The strain differs from known mesophilic *S. megasporus* in fatty acid composition, spore surface, aerial mycelia and optimum growth temperature and incubation period. The microorganism of the invention is also different from published information on the cultural and physiological characteristics of other known microorganisms.

The profile of the microorganism *Streptomyces megasporus* SD5 is given in Table I below:

TABLE 1

Profile of the thermophilic isolates

| Characters | Property of the thermophilic isolates |
| --- | --- |
| Substrate mycelia | Present, nonfragmented |
| Aerial mycelia | Present, short, septed |
| Spores in chains | Short chains and clusters |
| Spore surface warty | Ridges in mature spores |
| Mole % G + C | 69–70 |
| Cell wall chemo type | Type 1 (LL-DAP and Glycine) |
| Whole cell sugar pattern | No diagnostic sugars |
| 4 Mu linked enzyme substrates | Positive with phosphatases and Stearases |
| Fatty acid profile | Matching 82% with Streptomyces |
| 16 S r RNA | 95% matching with Streptomyces |

The microorganism of the invention is isolated from hot water sources and springs using a nutrient medium containing carbon and nitrogen sources in a definite ratio and inorganic nutrient salts. Preferably, the isolation of the microorganism *Streptomyces megasporus* SD5 is done using a solidifying agent in combination with the nutrient medium.

The carbon sources are selected from glucose, starch, sucrose and agricultural wastes while the nitrogen sources are selected from peptone, yeast extract, beef extract, malt extract, casein hydrolysates, haemoglobin and fibrin.

The solidifying agents are selected from agar and agarose and the inorganic salts are selected from salts of calcium sodium, potassium and magnesium. Examples of the nutrient medium comprises glucose in an amount of 0.2 to 1 g, yeast extract in an amount of 0.1 to 0.6 g, glycerol in an amount of 0.2 to 0.5 g, NaCl in an amount of 0.1 to 0.6 g and Agar as the solidifying agent or glucose in an amount of 1.0 g, L-asparagine in an amount of 0.5 g, yeast extract 0.5 g, peptone in an amount of 0.5 g and agar as the solidifying agent or starch in an amount of 2.0 g, casein in an amount of 1 g and NaCl in an amount of 0.5 g.

The microorganism *Streptomyces megasporus* SD5 can be mutated using conventional mutagens selected from the group consisting of N-methyl-N'-nitro-N-nitrosoguanidine, ethyl methyl sulfonate and exposure to UV radiation. It is observed that under specific conditions of incubation, the microorganism of the invention produces an extracellular caseinolytic and fibrinolytic enzyme, which is useful as a thrombolytic agent. The enzyme has been named as actinokinase and shows similar characteristics as known enzyme urokinase that is present in fetal kidney and human urine.

Preparation of enzyme actinokinase an be done by cultivating the microorganism *Streptomyces megasporus* SD5 or a variant or mutant thereof under aerobic conditions at a temperature in the range of 45° C. to 65° C. in an alkaline aqueous nutrient medium and recovering the enzyme by any known method.

The nutrient medium can comprise of carbon sources, nitrogen sources, mineral salts and trace elements and is at a ph of 7.5 to 9.0. The carbon source is selected from glucose, soluble starch and raw starch and the the nitrogen source is selected from yeast extract, peptone, tryptone, casein and casein hydrolysate. The inorganic salts used are selected from the group consisting of chlorides of calcium, sodium, potassium and magnesium. The trace elements are selected from the group consisting of iron, manganese, copper, zinc, borate and molybdenum.

During the production of the enzyme, the temperature is preferably maintained in the range of 50° C.–55° C. and the cultivation is carried out by fermentation, preferably submerged fermentation. During fermentation, an anti-foam agent, preferably soybean oil can be added to the nutrient medium. The enzyme can be concentrated with ammonium sulphate and then separated from other proteins by gel filtration, ion exchange chromatography and isoelectric focusing in the presence of a buffer having a pH in the range of 3–10.

The fermentation and production of the enzyme is monitored on solidified media by the clear zone (halo) formed on milk or fibrin agar or spectrophotometrically by monitoring the formation of the product of hydrolysis of casein or fibrin. Fractions eluted from Rotofor System using broad range ampholyte showing the enzyme activity are pooled together and dried in a Savant drier for storage and further use. Storage can be done at ambient temperature (~20–25° C.).

Analysis shows that the enzyme is a serine protease with a molecular weight of 35 kDa and has an optimum temperature of 55° C., pH optima of 8.0 and pI of 7.56. The process of production of the enzyme is relatively simpler and inexpensive when compared to processes for the extraction of prior art enzymes streptominase, staphylokinase or urokinase. The yield is also good. A comparison of prior art enzyme preparation processes and the process for the preparation of the enzyme of the invention is given in Table II below:

TABLE II

Comparison of enzyme preparation processes

| Enzyme | Substrate | Production time | Sp. Treatment after cell removal | Purification |
| --- | --- | --- | --- | --- |
| Streptokinase Staphylokinase | Brain, heart infusion broth | 24 h at 25° C. - 37° C. and pH 7.5 | Treatment at 75° C. and cetrimide treatment | Sepharose 4B Blue dextran Isoelectric focusing |
| Urokinase | Extraction from human | Temperature not given | Concentration with Amicon | Ion Exchange column |

TABLE II-continued

Comparison of enzyme preparation processes

| Enzyme | Substrate | Production time | Sp. Treatment after cell removal | Purification |
|---|---|---|---|---|
| | urine/fetal kidney | | filter at pH 6.5 | Dialysis Elution with NaCl at pH 9.1 |
| Actino-kinase (crude) | Special medium not necessary - different substrates can be utilized for enzyme production | 18 h at 55° C., pH 7–8.5 | Enzyme can be concentrated from cell broth by change in ionic concentration | Ion exchange column Dialysis Isoelectric focusing |

The above data when taken along with the activity profile in terms of in vitro clot lysis indicate that the enzyme acts on synthetic (200 μl oxalated plasma, 500 μl of sterile saline, and 200 μl of 0.25% $CaCl_2$, mixed and incubated at 37° C. for clot formation) and blood clot in both crude and purified form.

A comparison of the enzyme of the invention with available enzymes is given below in Table III.

TABLE III

Comparison of actinokinase with available enzymes

| Enzyme | Optimum Temperature | Optimum pH | E. C. No. | Mol. Wt. | Metal requirement | Proteolytic/non-proteolytic |
|---|---|---|---|---|---|---|
| Streptokinase Staphylokinase | 25–37° C. | 7.3–7.5 | 3.4.24.4 | 45–57 kDa Dimer | $Ca^{++}$, $Zn^{++}$ for stability | Non protease plasminogen activators |
| Urokinase | 37° C. | 7.5 | 3.4.21.73 U | 55–60 kDa monomer | Not mentioned | Proteolytic plasminogen activator |
| Actinokinase | 55° C. | 7–8.5 | 3.4.24.73 A | 35 kDa monomer | $Ca^{++}$ for stability | Proteolytic plasminogen activator |

The *Streptomyces megasporus* SD5 isolate was grown in GYP medium (glucose/yeast extract/peptone), pH 8.0 and maintained as spore suspension at −70° C. in the presence of 25% glycerol; a cryoprotectant (Hopwood et al 1985). For production of the enzyme, 100 μl of spore suspension was inoculated in 100 ml of sterile GYP medium, pH 8.0, containing (% w/v) glucose—1, yeast extract—0.5, peptone—0.5, NaCl—0.5 and $CaCl_2$—0.02 in a 500 ml Erlenmeyer flask and incubated for 18 h at 55° C. After cooling to room temperature the cells were harvested by centrifugation at 10000 g for 8 min and the spent broth was filtered through a 0.22μ membrane to remove the spores. The filtrate was concentrated by precipitating with 80% saturation of ammonium sulphate, dialysed and used as crude enzyme solution.

A strong fibrin-specific fibrinolytic enzyme was purified from the cell-free spent culture broth. The strain produced 150 mg crude protein $1^{-1}$ of spent broth, with a specific activity of 80 Plough units $mg^{-1}$, within 18 h of incubation at 55° C. in glucose yeast extract peptone medium, pH 8.0. For production of the enzyme, the strain utilized different carbon and nitrogen sources with a C:N ratio of~1:2. The enzyme was stable at a broad range of pH ranging from 5 to 9, and highly thermostable with 50% activity after storage 60° C. for 6 months. The enzyme belonged to the seine endopeptidase group. In vitro clot lysis revealed that the enzyme was active at 37° C.

Fibrinolytic Enzyme Assay

The fibrinolytic (thrombolytic) activity was assayed on solid and liquid media (Harverkate & Trass 1974, Lottenberg et al. 1981). The reaction mixture (1 ml) comprised of chromogenic substrates, such as benzoyl-β- alanyl-glycyl-arginine-ρnitroanilide (20 μmol $1^{-1}$) in 10 mM sodium phosphate buffer, pH 8.0 and incubated at 55° C. for 30 min after addition of 1 ml, enzyme solution containing 0.5 μg protein $ml^{-1}$, cooled to room temperature and the liberation of ρ-nitroanilide was measured by increased absorbance recorded at 405 nm using a UV-VIS Spectrophotometer (DU 8B, Beckman, Sweden). One unit of the enzyme was defined as the amount of enzyme that catalysed the formation of 1 ng of ρ-nitroanilide $min^{-1}$. The caseinolytic activity was determined by Dunn (1989) in terms of μmol tyrosine $min^{-1}$. Protein was determined using Folin Ciocalteau phenol reagent. All the results of growth and assays are the means of three separate experiments.

Effect of pH and Temperature on Production of the Fibrinolytic Enzyme

The optimum pH for enzyme production was determined at different pH values ranging from 5 to 9 using Citrate phosphate buffer, pH 5.0, Sodium phosphate buffer, pH 6.0–8.0 and Tris.HCl, pH 9.0–10.0. Stability to pH was determined by assaying the residual activity after exposure to different pH values ranging from 5.0 to 9.0. The optimum temperature for production was determined by assaying the enzyme activity at different temperatures ranging from 35° C. to 70° C. for 18 h using GYP medium, pH 8.0.

Effect of Growth Period on the Production of the Enzyme by *S. megasporus* SD5

To determine the amount of the fibrinolytic and caseinolytic enzymes through out the growth period of 24 h, quantivation of the enzymes was carried out as mentioned above along with the growth, in terms of protein, at definite intervals.

Effect of Different Storage Times, at Different Temperatures Ranging from 35° C. to 70° C. on the Activity of the Enzyme Thermostability was determined by measuring the residual activities after storing the enzyme for 6 months at different temperatures ranging from 35° C. to 70° C. The enzyme solution in 10 mM phosphate buffer, pH 8.0 was stored at different temperatures (35° C. to 70° C.) for different periods (1–6 months) and the residual activity was determined at definite intervals, as mentioned previously and compared with the activity of the enzyme solution (as 100%) kept at 4° C. as control.

Effect of Different Carbon and Nitrogen Sources Along with Inorganic Chemicals on the Production of the Enzyme by *S. megasporus* SD5.

The effects of different carbon and nitrogen sources as well as inorganic chemicals on the production of the enzyme were evaluated by supplementing the basal medium, pH 8.0 with different carbon and nitrogen sources followed by incubation at 55° C. for 18 h. The activities of the enzyme synthesized from different sources were compared with that of the control (GYP). Similarly the effects of different inorganic compounds on the synthesis of the enzyme were also determined.

Effects of Mutagenic Chemicals on the Synthesis of the Enzyme

To increase the synthesis of the enzyme, the spore suspension ($0.6 \times 10^5$) of S. megasporus SD5 was exposed to different mutagenic substances, such as, N-methyl-N-nitro-N-nitrosoguanidine (NTG), ethyl methane sulphonate (EMS) and u.v. (254 nm) irradiation for different periods as in the standard protocol (Hopwood el al. 1985). The mutant colonies were inoculated in GYP for production of the enzyme and amount of the enzyme produced was marginal.

Production of the Fibrinolytic Enzyme using S. megasporus SD5

Preparation of Seed Culture

After optimisation of the fibrinolytic enzyme at flask level, preparation of the seed culture was carried out. To prepare the seed culture, GYP medium, pH 8.0 (50 ml) containing 0.02% $CaCl_2$ was inoculated with 50 μl of spore suspension and incubated at 55° C. for 10 h and the resultant growth was used to inoculate 500 ml fresh pre-warmed (55° C.) GYP medium followed by incubation at 55° C. for 10 h.

Bench Scale Production of the Enzyme

In a laboratory scale (10 l) fermenter (MDL Marubishi, Japan) 5 l prewarmed medium (55° C.) was inoculated with 500 ml seed culture grown as mentioned earlier and incubation was continued for 18 h at 55° C. with agitation (150 rev $min^{-1}$) and aeration (400 ml $min^{-1}$). The fermented broth was cooled to room temperature and the density of the viable cells was determined. The cell mass was separated by centrifuigation at 10000 g for 10 min at 18° C. and the cell free spent broth was filtered through a 0.22-μm membrane to remove the spores. The protein was concentrated by precipitation with 80% saturation ammonium sulphate. The precipitate was dissolved in 100 ml of 10 mM phosphate buffer pH 8.0, dialysed against same buffer at ambient temperature for 12 h, freeze dried and used as crude enzyme preparation.

Gel Eletrophoresis

Post-eletrophoretic reactivity after non-denaturing PAGE was carried out according to Hames (1981) along with the standard proteins in duplicate. One part was stained with Coomassie Blue R 250 and the other part was incubated with a fibrin plate for 2 h at 37° C. and the fibrinolytic activity was detected as a clear zone after staining the fibrin plate with Coomassie Blue.

To determine the class to which the enzyme belonged the effect of different protease inhibitors were studied in detail. As the fibrinolytic enzyme could be used as a therapeutic agent for different types of thrombosis so in vitro clot lysis was studied with both natural and synthetic clots.

Effect of pH and Temperature on Production

Though the maximum production of the enzyme by Streptomyces megasporus SD5 was at a pH range of 7–9 with an optimum of pH 8.0 (FIG. 1). At pH 5.0 and pH 10 more than 50% of the optimum was produced. The residual activity of the enzyme after exposure to different pH values revealed that the enzyme retained 51% activity even at pH 5.0. The optimum temperature for the synthesis of the enzyme was 55° C. but the enzyme showed 66% activity at 37° C., at 60° C. more than 80% of the optimum was produced (FIG. 1).

Effect of Growth Periods on the Production of the Enzyme

Streptomyces megasporus SD5 produced a fibrinolytic enzyme at 55° C., after 9 h growth, which increased up to 18 h and then remained constant. Like other thermophilic Streptomyces strains, the growth of Streptomyces megasporus SD5 increased linearly up to 21 h followed by decrease up to 24 h (Chitte & Dey 2000). The caseinolytic enzyme, as a minor component, increased up to 24 h (FIG. 2), which seemed to be related with the growth cycle of the thermophiles. The production time (18 h) was comparable to other available enzymes (Jackson et al 1981). The specific activity of the cell free broth was 2.37 ng $μg^{-1}$ which increased to 4.2 ng $μg^{-1}$ after concentration. The clot lytic activity of the concentrated protein solution seemed to be 80 IU (Plough unit) $mg^{-1}$ of protein. So the strain seemed to be the stronger producer of fibrinolytic enzyme with comparison to others (Nakajima et al 1993).

Effect of Storage Times at Different Temperatures

Thermal stability was tested by measuring the residual activities at definite intervals after storing the enzyme for 6 months, both in solid and liquid forms, at different temperatures (35–70° C.) and comparing the residual activity with that of the control. The enzyme was stable for 6 months at 40° C. At 45° C. only 5% activity was lost after 6 months, 20% and 25% activity were reduced after storage at 50° C. and 55° C. respectively. At 60° C. 50% of the activity was retained after 6 months but at 65° C. more than 405 activity was lost even within 2 months and gradually decreased linearly with the storage time. At 70° C. most of the activity was lost within one month, only 22% activity was retained. This revealed that the enzyme was quite stable up to 60° C. (FIG. 3). Both in terms of thermostability and resistance to pH the enzyme was better than other enzymes (Castellino et al 1993, Barlow 1993)

Effect of Different Substrates on the Production of the Enzyme

The effects of different carbon sources on the production of the enzyme by S. megasporus SD5 showed though the organism could synthesize the enzyme with other media e.g. soybean meal, oat meal, glucose and malt extract and sucrose but GYP seemed to be optimal for production of the enzyme (Table IV). Though starch seemed to stimulate the synthesis of the enzyme by different bacteria and actinomycetales (Dolidze et al 1975, Vladimoriva & Kornienko 1987, Loginova et al. 1980) but for this thermophile starch did not exhibit any enhancing effect on the synthesis of the enzyme was inhibitory. This strain could utilize sodium citrate, sodium acetate, glycerol—arginine, fructose, mannose and arabinose to produce enzyme in the range of 60 to 70% of the optimum but utilization of dextran, rhamnose and lactose could only 40% enzyme. It was observed that out of all cations only $Ca^{++}$ enhanced activity (not included in the diagram) by up to 20%.

As nitrogen sources, peptone and yeast extract seemed to be effective for production of the enzyme (76% and 67% of the control), containing both yeast extract and peptone (Table V). The result corroborated the previous observation by Bascaran et al (1990). In the presence of haemoglobin and fibrin, though costly, the isolate could synthesize 4 to 10% more enzyme than the control. Casein and casitone were also suitable for enzyme production (77%–78%). Potassium nitrate, elastin, methionine and phenyl alanine might not be the suitable substrates as S. megasporus SD5, as it could produce only 33% to 45% of the maximum activity. With ammonium sulphate only 11% of the control was produced though by others it has been found to be an enhancer of synthesis of protease (Egorov et al. 1987). It was reported by Loginova et al (1980) that trace metal solution and phosphate enhanced the production of different proteses, but these could not increase the production of the thrombolytic enzyme by S. megasporus SD5.

As production medium GYP, pH 8.0, supplementation with NaCl and $CaCl_2$ seemed to be optimal for the production of the fibrinolytic enzyme by S. megasporus strain SD5.

The elemental analysis of all media containing different concentrations of glucose and peptone/yeast extract, revealed that for optimum synthesis of the enzyme by S. megasporus strain SD5, a definite C:N ratio 3.8:7.0 (~1:2) was necessary.

In the bench scale fermenter S. megasporus SD5 produced 150 mg $l^{-1}$ of crude enzyme with a specific activity of 4.2 ng $\mu g^{-1}$ protein which was equivalent to 80 IU (Plough unit) $mg^{-1}$ when compared with the standard enzyme obtained from the National Institute for Biological Standards and Controls, Hertfordshire, UK, resulting more than 12000 IU $l^{-1}$ of the spent broth. Compared to other fibrinolytic enzymes available in the market this enzyme seemed to be definitely cheaper.

Post-electrophoretic Reactivity

Post-electrophoretic reactivity of a native gel on a fibrin plate revealed an active polypeptide chain with a molecular weight of ~35 kDa (FIG. 4). From the clear zone in substrate gel, the strong activity of the enzyme could be predicted. The effects of various inhibitors on fibrinolytic activity of the enzyme are summarized in FIG. 5. Antipain, bestatin, pefabloc, aprtinin, PMSF, chymostatin strongly repressed the activity. These are serine peptdase inhibitors indicating that the enzyme belonged to serine peptidase group. The enzyme was moderately sensitive to leupeptin, trypsin inhibitor and TPCK No change in the activity in presence of phosphoramidin and 1,10 phenanthroline removed the possibility of the enzyme being a metallo protease. The enzyme was neither a cysteine nor an aspartate peptidase. Reversion of inhibitory effect of EDTA with addition of $Ca^{++}$ revealed that metal was required for thermostability.

In vitro clot lytic effect of the enzyme, using glass bead experiment (Plough & Kjeldgaard 1957), showed that the enzyme could lyse both natural clot of plasma as well as synthetic clot of fibrinogen, plasmin, $Ca^{++}$ and thrombin within 30 min.

The enzyme could prevent re-occlusion also. S. megasporus SD5 could produce a crude fibrinolytic enzyme (150 mg $l^{-1}$) within a short period of 18 h at 55° C. The strain could utilize different media for synthesis of the enzyme though a defined media GYP with $Ca^{++}$ was optimum for production of the enzyme. Due to thermostability, resistance to a broad range of pH and higher shelf life at ambient temperatures makes the enzyme cheaper than the available fibrinolytic enzymes.

TABLE IV

Effects of different carbon sources on the production of fibrinolytic enzyme by S. megasporus SD5

| Sources | Conc (% w/v) | Protein con. (mg 100 $ml^{-1}$) | Relative Fibrinolytic activity (%) |
|---|---|---|---|
| Basal medium | — | — | — |
| Dextran | 1 | 3.5 ± 2.1 | 40 |
| Oatmeal | 5 | 4.3 ± 1.8 | 28 |
| Meat extract | 5 | 3.7 ± 0.9 | 38 |
| Soybean meal | 5 | 4.7 ± 1.9 | 70 |

TABLE IV-continued

Effects of different carbon sources on the production of fibrinolytic enzyme by S. megasporus SD5

| Sources | Conc (% w/v) | Protein con. (mg 100 $ml^{-1}$) | Relative Fibrinolytic activity (%) |
|---|---|---|---|
| GYP | Text | 10.56 ± 0.5 | 100 |
| Malt extract | 5 | 6.9 ± 1.3 | 48 |
| Glycerol-arginine | 1 | 9.6 ± 3 | 82 |
| Lactose | 1 | 3.5 ± 0.9 | 40 |
| Arabinose | 1 | 5.3 ± 2 | 60 |
| Sucrose | 1 | 6.2 ± 0.8 | 70 |
| Na - acetate | 1 | 4.8 ± 3 | 62 |
| Fructose | 1 | 5.5 ± 2.6 | 69 |
| Na-citrate | 1 | 4.6 ± 2.1 | 66 |
| Mannose | 1 | 3.6 ± 3 | 62 |
| Starch | 1 | 3.2 ± 0.5 | 41 |
| Rhamnose | 1 | 2.1 ± 2 | 39 |

Basal medium contained (% w/v) peptone 0.5, yeast extract 0.5, NaCl 0.5, $CaCl_2$ 0.2

Each experiment was carried out in triplicate and the results are shown as the mean ±SD from three different analyses. The values were compared by 't' test using SPSS for Windows, version 7.5, SPSS INC, USA 1989 (t=2.761–3.156,p=0.001–0.002).

TABLE V

Effects of different nitrogen sources on the production of fibrinolytic enzyme by S. megasporus SD5

| Sources | Conc (% w/v) | Protein conc. (mg 100 $ml^{-1}$) | Relative Fibrinolytic activity (%) |
|---|---|---|---|
| Basal medium | — | — | — |
| Peptone | 0.50 | 10.45 ± 10.4 | 78.2 |
| Yeast extract (TE) | 0.50 | 9.0 ± 0.2 | 67.2 |
| Peptone + YE | 0.50 | 10.56 ± 10.5 | 100 |
| Elastin | 0.10 | 7.5 ± 0.8 | 41.7 |
| $\alpha(NH4)_2$ butyric acid | 0.50 | 4.5 ± 1.0 | 37.4 |
| Casein | 0.10 | 10.45 ± 2 | 77.7 |
| Casitone | 0.10 | 6.32 ± 0.7 | 78.1 |
| Fibrin | 0.10 | 10.8 ± 2 | 110.9 |
| $(NH4)_2SO_4$ | 0.25 | 3.5 ± 3 | 11.0 |
| Haemoglobin | 0.10 | 9.64 ± 0.9 | 104 |
| K-nitrate | 0.10 | 4.2 ± 0.9 | 45.4 |
| L-methionine | 0.50 | 3.3 ± 2 | 36.4 |
| Phenyl alanine | 0.50 | 2.8 ± 2 | 36.2 |

BM=Basal Medium Contents (% w/v) glucose 1, NaCl 0.5, $CaCl_2$.02. Each experiment was carried out in triplicate and results are shown as the mean ±Sd from three different analyses. The values were compared by 't' test using SPSS for Windows, Version 7.5, SPSS Inc., USA, 1989 (t=2.980–3.982,p=0.002–0.003

Prior art enzymes show exhaustion of the inhibitor as a result of the neutralization by the $\alpha_0$-antiplasmin of the initially formed plasmin resulting in no or reduced action on the thrombus. Once the inhibitor gets exhausted the residual plasmin degrades several plamin proteins causing a tendency to bleeding. The activity and efficacy of prior art proteins is therefore limited. However, the enzyme of the invention does not show any of these disadvantages. Another advantage of the actinokinase enzyme of the invention is the less number of amino acids and gene length enabling easier modification. Also allergic reactions were not observed unlike in the use of streptokinase and staphylokinase (due to their pathogenic nature resulting in the formation of antibodies in patients). Table VI gives a comparison of the physicochemical and genetic properties of the prior art fibrinolytic systems and the enzyme of the invention.

TABLE VI

Comparison of the physicochemical and genetic properties of the prior art fibrinolytic systems and the enzyme of the invention.

| Fibrinolytic system | Mr (kDa) | No. of amino acids | Catalytic traid | Plasma cone (%) | Gene length (Kb) |
|---|---|---|---|---|---|
| Plasminogen | 92 | 790 | HIS, Asp, Ser | 200 | 52.5 |
| Plasmin | 85 | 715 | HIS, Asp, Ser | — | — |
| t-PA | 68 | 530 | HIS, Asp, Ser | 0.005 | 36.6 |
| Scu-PA | 54 | 411 | HIS, Asp, Ser | 0.008 | 6.4 |
| Actinokinase | 35 | 264 | HIS, Asp, Ser | ND | <2 |

Immunological responses in rabbits showed that the enzyme was non-allergenic and also exhibited no effects on plasma proteins. Thus actinokinase markedly reduces antibody induction without affecting the thrombolytic potency. Comparison of the N-terminal of actinokinase with those of relative serine proteases showed that it matched 85% with chymotrypsin, >75% with streptokinase, and 63% with urokinase indicating that the enzyme belongs to the chymotrypsin group and prokaryotes.

Since Actinokinase is a prokaryotic protein the potential for allergenic reactions in patients exists. The antigenicity, immunogenicity of actinokinase on rabbits and effects on blood cells and proteins was tested.

The immuno-reactivity of actinokinase was negative and the activity/antigen ratio was also less. Thus actinokinase could markedly reduce antibody induction without affecting the fibrinolytic potency. Minimum effective dose and no adverse effect could be compared with the single chain form of urokinase, which is a proenzyme, relatively fibrin specific both in vitro and in vivo (Gurewich et al 1984) and does not form complexes with plasma inhibitors (Pannell et al 1986). Since origins of streptokinase and staphylokinase are pathogenic, preformed levels of anti streptokinase and anti staphylokinase anti-bopdies are generally present in the patient's body (Vanderschueren et al 1994, Eliott et al 1993) resulting in allergic reaction. Actinokinase exhibited no adverse effects on animals.

Another set of experiments was run to test the activity and side effects of actinokinase. Urokinase, fibrinogen, thrombin and plasminogen were purchased from Sigma Chemical Co., St. Louis, USA. Chromogenic substrates, protease inhibitors and universal protease substrate were purchased from Roche Chemicals, Germany and other reagents, of analytical grade were obtained from the local market, All ampholytes, catholyte and anolyte were purchased from Bio-rad, California USA. Sodium phosphate buffer (10 mM), pH 8.0 was used through out the experiment, otherwise mentioned.

Enzyme Assay

The thrombolytic activity was measured on standard fibrin plate using the method of Haverkate-Trass (1974) as mentioned previously and compared with available thrombolytic enzyme, urokinase. Each sample (20 μl) was put on the fibrin clot layer and incubated at both 55° C. and 37° C. for 8 h. The zone of clear areas for standard urokinase and the enzyme of the invention was measured and thrombolytic activities of both enzymes were expressed in terms of Plough units. Amidolytic activity was determined using chromogenic substrates and one unit of activity is defined as the amount of enzyme, which released 1 mole of pNA min$^{-1}$. Amydolytic activity in liquid medium was determined using the method by Lottenberg et al (1981). Caseinolytic activity was assayed by the procedure described by Pokorny et al (1979). Protein concentration was estimated by a modification of the Lowry's method (1951).

Enzyme Purification

All steps for isolation and purification of the enzyme from the spent broth of *Streptomyces megasporus* strain SD5 were carried out at ambient temperature using 10 mM sodium phosphate buffer pH 8.0, unless mentioned. During purification the specific activity of the enzyme was expressed in Plough unit (Plough and Kjeldgaard 1957). The soluble proteins from the cell free broth were concentrated by fractional precipitation with addition of ammonium sulphate (30 to 80%) saturation. The precipitate at each step was collected by centrifigation at 15000 g for 10 min at 4° C. and dissolved in buffer, dialyzed at 4° C. for 24 h. The protein content and the activity of each sample were determined. The dialysate was put on a previously equilibrated Sephadex G-10-120 column (2×20 cm) with 10 mM phosphate buffer and the active proteins were eluted at 0.2 ml min$^{-1}$ and pooled together, concentrated by freeze drying and fractionated using a standard chamber of Rotofor System and a broad range biolyte (pH 3–10) (Bio Rad, USA). The active fraction and the neighbouring 2 fractions were collected and isoelectric focussing was repeated using a narrow range (pH 6.9–8.2). Rotolyte buffer containing AMPSO and 0.2 M β-picoline. For isoelectric focussing the sample was prepared as follows, 3 ml ampholyte and 54 ml of Milli Q water was mixed and run for 1 hr for stabilization, then 1 ml protein was added focussed for 6 h. The active fraction and the neighbouring two fractions were pooled together, concentrated and further purified by preparatory PAGE using Mini Prep Gel Electrophoresis system (Bio-Rad). The equipment used for purification of the thrombolytic enzyme are given in FIG. 6a and FIG. 6b. Homogeneity of all fractions were determined by PAGE at each step.

Zymography

After running a native PAGE (Hames 1981) with 4.5% stacking gel and 10% separating gel, gel was incubated at 55° C. on agar plates containing chromogenic substrates in a moist atmosphere until haloes appeared. For visualisation of the lysis the chromogenic plates were washed with 1% p-di methyl amino cinnamaldehyde (Roth and Levin 1989).

Determination of Molecular Weight

Sodium dodecyl sulfate acrylamide gel electrophoresis (SDS-PAGE) was performed on 12% gels following the method of Laemmli (1970). Gels were stained with Coomassie Brilliant blue R 250. The protein standards used for determining molecular weight included bovine serum albumin (66 kDa), pyruvate kinase (58 kDa), ovalbumin (45 kDa), glyceraldehydes 3-phosphate dehydrogenase (36 kDa) and trysinogen (24 kDa). The Gel filtration experiment was repeated using 12% gel and the same marker proteins.

Properties of the Enzyme

Effects of pH on Activity and Stability

The effects of pH on thrombolytic activity were observed using reaction mixtures of different pH Sodium phosphate (pH 5.0–7.0), Tris.Cl (pH 7.5–9.0), Carbonate-bicarbonate (pH 9.5–10) containing 0.2 mM Chromozyme U and 100 μl enzyme incubated for 30 min at 55° C. The enzyme activity was measured as increase in absorbance at 405 nm using an UV-VIS Spectrophotometer, (Chemito 2600, India) and expressed as units. To determine the pH stability, the enzyme was exposed to different pH for 30 min at 55° C. followed by determination of the residual activity after addition of substrates.

Effects of Temperature on Activity and Stability

The enzyme in the reaction mixture was incubated at pH 8.0 for 90 min at different temperatures ranging from 35° C. to 70° C. to determine the thermal stability. Maximum activity was expressed as 100% and the others were compared to the maximum activity. Residual activity was determined at 55° C.

Substrate Specificity

Substrate specificity of the enzyme was assessed at 405 nm by using various synthetic peptide substrates, (20 µM tagged with p-nitrandide acetate and resorufin, in the reaction mixture. The Michaelis constant (Km) was determined using Chromozyme U as substrate using line weaver Burk plot method (Jayaraman 1985).

Effects of Addition of Plasminogen on Enzyme Activity

To determine the role of plasminogen on the enzyme activity was determined in the cuvette at 55° C. in presence and absence of plasminogen. During running the experiment (100 µl) plasminogen (0.2 mM) was added in the experimental tube after 15 and 25 mins, incubated further and the activity was determined.

Effects of Inhibitors and Metal Ions on Enzyme Activity

Different protease inhibitors were separately dissolved in distilled water/methanol/dimethyl sulphoxide as per manufacturers protocol, so that final concentration of each inhibitor was 1 mM. The enzyme (50 µl) was mixed with same amount (50 µl) of inhibitor and incubate at ambient temperature for 30 min. The residual activity was measured at 55° C. as above using universal protease substrate and compared with that of the control without any inhibitor and the inhibition was determined as percentage taking control as 100% positive. Similarly the effects of metal ions (0.1 mM) on enzyme activity were also investigated using $Mg^{2-}$, $Co^{2+}$, $Hg^{2+}$, $Cu^{2+}$, $Fe^{3+}$, $Zn^{2+}$ and $Ca^{2+}$.

Proteolytic Activity

To determine the adverse effect of the enzyme on plasma protein. The enzyme (50 µg $ml^1$) was incubated with different plasma proteins (0.2 mg $ml^{-1}$) at 37° C. in 10 mM phosphate buffer Saline (PBS) buffer, pH 7.5 for 30 min. Control sets were incubated with substrates only along with the experimentals. The proteins were precipitated with 10% TCA, centrifuged. The activities on different proteins were determined at 280 nm except of haemoglobin and fibrin blue, which were determined at 580 and 650 nm respectively. The ratio of fibrinolytic and caseinolytic activities of the enzyme was compared with those of other known enzymes.

Amino Acid Composition of the Enzyme

The purified protein was hydrolysed in a sealed container under HCl vapour at 110° C. for 20 h, cooled to room temperature and filtered through a whatman filter paper and the precipitate was washed repeatedly with water. The resulting solution was concentrated using a rotary evaporator and extracted with chloroform and the composition was measured at 220 nm using a reverse phase HPLC system.

Amino Acid Sequence of the N-terminal of the Enzyme

The purity of the enzyme was checked using HPLC (Kim et al 1997). The lyophilised enzyme was dissolved in 2 ml 5% acetic acid and applied to a high performance liquid column chromatography with a LICHROSORB reverse phase C18 column (0.5×5 cm) at a flow rate of 0.3 ml $min^{-1}$. The column was washed with the 5% acetic acid and the enzyme was eluted using a gradient of 0.1% Trifluoro acetic acid in 0.1%/acetonotrile. The thrombolytic activity of the enzyme obtained from peak of HPLC was checked on fibrin plate.

The protein on SDS-PAGE gel was electroblotted to a polyvinylidene difluoride membrane (PVDF: Bio-Rad) by cutting the membrane to the same size as the gel and wetting with 100% methanol for 2–3 seconds, rinsing with water for 2–3 minutes and equilibrating in transfer buffer 10 mM 3-Cyclohexyl amino-1-propane sulfonic acid (CAPS), pH 11.0 containing 10% methanol for 30 min. The electrophoresed gel was rinsed in transfer buffer for 5 min. The gel and the PVDF membrane was sandwiched in between. Whatman 3 mm paper and placed in the blotting cassette with a backup membrane. The transfer was carried out at 0.5 A constant current for 8–10 h. After transfer, the membrane was rinsed several times with Milli-Q water to remove the buffer salts followed by fixation with 100% methanol for 2–3 seconds. The blot was stained with 0.2% Ponceau S in 1% acetic acid. The stained protein was marked with a pencil and destained using 50% methanol, rinsed several times with water, air dry, excise the protein band and sequenced using a Shimadzu model PPSQ-10 gas phase sequencer consisting of an Edman reaction unit, an on-line PTH analyser and a CR-7A data processor in National Facility for photolabelling and peptide Sequencing in Biomolecular System, IIT, Powai, Mumbai.

A database searching program called SWISSPROT (Altschul et al 1997) was used to compare theoretical spectra of peptides in the known databases with experimental data for unknown peptides. This was carried out in the Bioinformatic Department, Pune University.

Purification

The concentrated and dialysed thrombolytic enzyme was purified from the cell free broth of *S. megasporus* strain SD5 to electrophoretic homogeneity in four steps using column chromatography, primary and secondary isoelectrical focussing and Preparatory PAGE and the purification process was summarized in (Table VII). Filtration through the sephadex column yielded one major peak in between $15^{th}$ and $25^{th}$ fractions showing thrombolytic enzyme with a specific activity of 33682 PU $mg^{-1}$ protein. This result indicated that the enzyme did not bind to the column. The purity of the enzyme solution was improved further by isoelectric focussing. A single peak within $8^{th}$ and $12^{th}$ fractions (pH 7 and pH 8) with an activity of 78400 U $mg^{-1}$ was obtained in the fraction between (FIG. 6). Further purification was obtained with a specific activity of 95300 U $mg^{-1}$ after second focussing with short-range rotolyte which was further enhanced to 236550 U $mg^{-1}$ after preparatory PAGE. The yield of the pure enzyme was 9.9 mg with 55 fold purification. The high purity of the enzyme was demonstrated by the detection of a single band on PAGE (FIG. 7). With gel filtration same molecular weight of the enzyme was obtained (FIG. 8). The pure protein showed a single peak at 220 nm with HPLC. The enzyme was a monomer with a molecular weight 35 kDa.

TABLE VII

Purification profile of the thrombolytic enzyme

| Fractions | Total Vol. (ml) | Total protein (mg) | Specific activity (U $mg^{-1}$) | Purification (fold) | Yield (%) |
|---|---|---|---|---|---|
| Broth | 7000 | 1510 | 4530 | 1 | 100 |
| Amm. Sulfate | 100 | 1470 | 5880 | 1.3 | 97.4 |
| Dialysis | 100 | 1445 | 21675 | 4.78 | 95.7 |
| Sephadex-G-10-120 | 50 | 980 | 33682 | 7.44 | 64.9 |
| Rotofor ($1^{st}$ fraction) | 9 | 850 | 78400 | 17.31 | 56.29 |
| Rotofor $2^{nd}$ Fraction | 10 | 760 | 95300 | 21.04 | 50.33 |
| Prep. PAGE | 6 | 150 | 236550 | 55.22 | 9.93 |

Effects of pH on Thrombolytic Activity and Stability of the Enzyme

Effects of pH on the activity and the stability of the enzyme were studied in the range of 5 to 10 (FIG. 9). Though the enzyme showed optimum activity at pH 8 but from the graph it can be seen that the enzyme was active (>50%) at pH of 5 and at pH 10, 65% activity was present. The pH stability of the enzyme also studied after incubation at each pH for 30 minutes which showed that the enzyme was quite stable at pH 7 to 9. After exposure to pH 5 and 6 the residual activities were 55 and 70% of control were retained respectively. Exposure to pH 10 retained more than 60% activity.

Effects of Temperature on the Activity and Stability of Actinokinase

Effects of temperatures on the activity and the stability of the enzyme were studied in the range of 35° C. to 70° C. Optimum temperature for the activity of the enzyme was 55° C. (FIG. 10) but the enzyme exhibited more than 90% activities at 50° C. and 60° C. and >75% activity was present at both 45° C. and 65° C. At 37° C. the enzyme exhibited about 65% activity.

The thermostability studies indicated that the residual activities of the enzyme after exposure to 35° C. and 55° C. for 90 min were same as that of control (FIG. 11) showing that the enzyme was quite stable up to 55° C. The residual activity at 60° C. was same at that of control up to 30 min, further exposure for 90 min reduced the activity (5 to 10%). After exposure to 65° C. and 70° C. the initial activities were 85% and 70% of the control within 30 min and only 45% and 25% activities were present respectively after 90 min exposure.

Substrate Specificity

Amydolytic Activity of the Enzyme

The enzyme appeared to have broad substrate specificity for synthetic peptides. The relative activity of the purified enzyme against a range of synthetic nitranilide peptides was shown in (Table VIII). It was observed that the thrombolytic enzyme was most active with Benzoyl-β-ala-gly-arg-pNA, like urokinase. With all other peptides the enzyme could hydrolyse the -gly-arg- more (76–80%) and moderately (54%) when only -arg- was present and with -ala-arg- it showed only 29–31% activity. The enzyme exhibited least activity with a peptide chain of -prol-arg or lys-arg.

The enzyme could cleave Benz-β-ala-gly-arg-ρNA very strongly and completely cleaved peptides containing gly-arg-ρNA. The enzyme could not hydrolyse lys -ρNA and showed weak activity on phe-arg and prolyl-arg containing peptides. The low Km value of the enzyme was 2.2 μM/min/ml with chromozyme U as substrates showing the enzyme efficiency even in absence of plasminogen.

TABLE VIII

Actinokinase activity on different synthetic peptides

| Substrates | Activity (Uμg$^{-1}$) | Relative activity % |
|---|---|---|
| N-α-Benz-L-arg-pNA | 2.3 | 54 |
| D-Val-cyclohexyl-Ala-arg-4-pNA (di) (Chromozyme GK) | 1.2 | 28 |
| Benz-pro-phe-ala-arg-4-PNA (Chromozyme PK) (SEQ ID NO.:1) | 1.3 | 32 |
| Tosyl-gly-pro-lys-4- (Chromozyme PL) | 0.84 | 20 |
| Tosyl-gly-pro-arg-4-pNA (Chromozyme TH) | 0.25 | 56 |
| N-met-sulf-D-phe-gly-arg-4-pNA (Chromozyme t-PA) (SEQ ID NO.:2) | 3.28 | 78 |
| Carbobenz-val-gly-arg-4-pNA (Chromozyme TRY) | 3.40 | 81 |
| Benzoyl-β-ala-gly-arg-4-pNA (Chromozyme U) | 4.2 | 100 |

TABLE VIII-continued

Actinokinase activity on different synthetic peptides

| Substrates | Activity (Uμg$^{-1}$) | Relative activity % |
|---|---|---|
| N-Methoxy-bonyl-D-Norleu-gly-L-arg-4-pNA (Chromozyme X) | 3.2 | 76 |
| N-(resor-4-carbonyl)-Piperi-4-carbonic acid (Universal protease) | 3.9 | 93 |

Substrates (0.2 mM) were incubated at 55° C. and the activity was determined at 405 nm after 30 min incubation as above. All experiments were carried out in triplicate.

Effect of Plasminogen Addition on Amidolytic Activity of the Enzyme

Amydolytic activity exhibited by the enzyme was same in presence and absence of plasminogen. Addition of plasminogen at different intervals could not enhance the activity.

Similar results were obtained when tested on fibrin plates with and without plasminogen. So it could be concluded that the enzyme was fibrinolytic but plasminogen independent.

Effects of Inhibitors and Metal Ions on the Enzyme Activity

Antipain, Bestain, Pefabloc, Aprotinin, PMSF, Chymostatin, the serine protease and trypsin inhibitors (Katunama et al 1983), highly repressed the enzymatic activity. The enzyme was moderately sensitive to leupeptin, trypsin inhibitor, TPCK. No change in activity in presence of phosphoramidin, 1,10 phenanthroline which removed the possibility of the enzyme being a metallo protease. Insignificant inhibition by E-64 and β-mercaptoetianol and pepstatin revealed that the enzyme might not a cysteine peptidase, neither a cysteine nor an aspartate protease. Except $Ca^{2+}$, other divalent cations did not exhibit any effects on the activity. The inhibitory effect of EDTA could be reverted back by addition of $Ca^{2+}$ in the enzyme solution containing EDTA which showed that $Ca^{2+}$ was required for activity at 55° C. as $Ca^{2+}$ was known to stabilize the enzyme protease (Lee et al 1996) which maintained the thermostability.

Proteolytic Activity

The proteolytic activities of the purified enzyme on blood proteins as well as on other proteins were studied using fibrinogen, thrombin, bovine albumin, haemoglobin, casein, streptokinase, trypsin heparin and chymotrypsinogen. The proteoiytic activity of the enzyme with bovine serum albumin, haemoglobin, fibrinogen and thrombin varied from 5–30% of the control. The enzyme was active in presence of streptokinase, heparin and trypsin. With casein as the substrate, the activity was $1.0 \times 10^2$ μmole/tyrosine mg$^{-1}$ protein min$^{-1}$. For comparison of the activity control, as suspension of fibrin clots in buffer solution, was incubated with the enzyme and the proteolytic activity was measured as per Dunn (1989). The fibrinolytic activity seemed to be $1.0 \times 10^3$ μmole/ tyrosine mg$^{-1}$ protein min$^{-1}$. The ratio of the fibrinolytic and caseinolytic activity was about 10:1 which might be good for fibrinolytic activity (Kim et al 1996). Same results were obtained on the plate assay on the fibrin plate a clear zone gradually increased with time whereas caseinolytic zone was same.

Amino Acid Composition of the Enzyme

One of the most striking features of the enzyme is that all amino acids are hydrophilic in nature (Table IX). It is believed that the high concentration of alanine, proline and tryptophane are responsible for anchoring the enzyme on the target. The enzyme did not show any affinity for plasminogen so increase in affinity for lysis be due to "Surface assembly" on the fibrin surface via the binding site of these residues like lysine binding site of plasmin (Wiman and Wollen 1977). It was also noted that the enzyme also contained the common catalytic triad "Serine, His and Asp" like other serine peptidases, which might prove the similarities in the reaction mechanism of different serine peptidases with different evolutionary origins (Nelles et al 1990). Most probably like other chymotrypsin helped out of 3 residues, serine might make nucleophilic attack, His might act as catalyst and Asp to keep the position of His with serine.

TABLE IX

Amino acid composition of actinokinase, Per 100 residues

| ASP | 3.7 | Val | 9.0 |
| --- | --- | --- | --- |
| Glu | 4.1 | Pro | 14.1 |
| Asn | 3.1 | Trp | 10.5 |
| Glu | 3.1 | Phe | 2.9 |
| Ser | 6.2 | Ile | 1.4 |
| Thr | 5.1 | Leu | 7.2 |
| Gly | 3.8 | Arg | 2.8 |
| Ala | 10.7 | His | 9.3 |
| Tyr | 3.0 | | |

Sequence of the N-terminal of the Enzyme

It was observed that the activity of the enzyme was more than (85%) after carbonylpeptidase treatment where as aminopeptidase treatment reduced the activity drastically (<10%) so the sequence of N-terminal of the enzyme was compared with the available thrombolytic enzymes. The N-terminal amino acid sequence of the first 16 residues of actinokinase (EC. 3.4.21.23) was D-E-N-Q-S-T-G-A-Y-V-P-P-Y-F-I-L (SEQ ID NO.:3) which was identical with only chymotrypsin. Protein similarity of the thrombolytic enzyme with the sequence of other serine peptidases revealed that the sequence was matching 87–100% with (3 amino acids overlapped) Chymotryspins from different sources showing that the enyzme belonged to chymotryspin group, it is matching with 74% with (4 amino acid overaped) streptokinase which might show the prokaryotic origin and it was matching with 63% with (8 amino acids overlapped) urokinase of different sources. So it could be concluded that the sequence was unique and not homologous with other enzymes.

While the exact mode of action of actinokinase is not known it is believed that actinokinase diffuses in the blood clot through the light region and attacks the connector rods of fibrin molecule and cleaves fibrin chain randomly after arg-val subunits. Each target fibrin unit contains at least 360 positively charged aminoacids, projected from surface to interact with the surrounding solvent and accessible to cleavage.

Without wishing to be bound by any theory, it is believed that the mechanism of action of the enzyme is as follows. The alternate light and dense regions of the fibrin monomer allow the enzyme to diffuse into the interior of the blood clot and to destroy the fibrin filaments by attacking their accessible connector rods. It is believed that the enzyme of the invention, cleaves the fibrin chains randomly after -arg-val subunits. Each target fibrin unit contains a total of 360 positively charged amino acids whose exact positions are not known. It is believed that these units project from the surfaces of the fibrin to interact with the surrounding solvent and are therefore potentially available for cleavage. Actual cleavage at particular points occurs very rapidly— particularly at the connector region, in particular where the triple helical is disrupted. This could be due to the surface assembly of the enzyme on the fibrin surface due to lysine binding sites.

The invention will be explained in greater deal with reference to the following examples which should not however be construed as limiting the scope of the invention since they are illustrative.

EXAMPLE 1

A. Isolation of *S. megasporus* strain SD5 from Hot Spring Water a. Preparation of Nutrient Solution Medium 1

Glucose 0.5 g

Yeast extract 0.5 g

Glycerol 0.5 g

NaCl 0.5 g

Agar 2 g

Distilled water 100 ml, pH 7.0–9.0

Medium 2

Glucose 1.0 g

L-asparagine 0.5 g

Yeast extract 0.5 g

Peptone 0.5 g

Agar 2.0 g

Distilled water 100 ml pH 8.0–9.0

Medium 3

Starch 2 g

Casein 1 g

NaCl 0.5 g

Distilled water 100 ml pH 7 were cooled to 45° C., poured into petri plates and allowed to stand.

b. Preparation of Water Samples

Water samples (100 ml) from hot springs were kept at 80° C. for 1 hour. After cooling, the samples were filtered through a membrane filter and were used to inoculate each of the above mentioned isolation media one at a time. The membrane was suspended in dilute saline and thoroughly shaken for 15 minutes and the washed water was used to inoculate the plates by spreading thoroughly. The inoculated petri plates were inoculated at 55° C. for 48 hours.

Growth of *Streptomyces megasporus* SD5 was observed with elongate colourless branched substrate mycelia and short aerial mycelia.

B. Cultivation of *S. megasporus* SD5 for the Fermentative Production of Fibrinolytic Enzyme Actinokinase

*S. megasporus* strain SD5 was maintained on glucose yeast extract medium. The spores were collected in water by scraping the agar surface, filtered and centrifuged at 8000 g for 10 minutes. The spores were stored at −70° C. in the presence of a cryoprotectant. The organism was also maintained on slants of the above mentioned medium.

Flask Level Production

One litre of glucose yeast extract peptone medium was inoculated with 100 µl of spore suspension of *S. megasporus* SD5, incubated at 55° C. for 18 hours, cooled, spun and filtered through 0.22μ Millipore membrane. The enzyme activity of the broth was assayed.

Fermenter Level Production

The glucose yeast extract medium (70 ml) was sterilized and inoculated with the spore suspension and incubated on a shaker incubator. The resultant growth was used to inoculate 700 ml of prewarmed production medium in 7 flasks and incubated for 12 hours. The resultant growth was used to inoculate 7 litre prewarmed medium in a 10 l laboratory scale fermenter (Marubishi, Japan) with an air flow of 400 ml min$^{-1}$ and agitation of 150 rpm and incubated for 24 hours at 55° C.

The aliquots of culture filtrate were collected time to time and tested for the quantity of the enzyme. The cell free spent broth containing enzymes was obtained after separating the cell masses by centrifugation at 8000 g for 10 minutes at 4° C. and further processed as described in step C below. The same procedure was repeated with different mutants and variants of S. megasporus SD5 resulting in differences in production of the enzyme.

C. Purification of the Fibrinolytic Enzyme

The protein from the cell broth was precipitated with 65% saturation of ammonium sulphate. The precipitate was dissolved in minimum amount of phosphate buffer, pH 8.0 and dialysed. The dialysed sample was passed through a Sephadex G-10–20 column (20*100 mm) and eluted with a gradient (0.01 M to 0.1 M). The eluted material was then fractionated using Standard Chamber of Isoelectric Focusing System using a voltage of 600–3000 V for 4–5 hours, other conditions being kept according to manufacturers protocol.

The fractions with activity were pooled together and the activity checked at each step. The electrophoretically homogenous protein was taken as the enzyme solution. A total of 2.4 units was available with nearly 65% yield.

EXAMPLE 2

*Streptomyces megasporus* SD5 isolate was grown in GYP medium (glucose/yeast extract/peptone), pH 8.0 and maintained as spore suspension at −70° C. in the presence of 25% glycerol; a cryoprotectant (Hopwood et al 1985). For production of the enzyme, 100 μl of spore suspension was inoculated in 100 ml of sterile GYP medium, pH 8.0, containing (% w/v) glucose—1, yeast extract—0.5, peptone—0.5, NaCl—0.5 and CaCl$_2$—0.02 in a 500 ml Erlenmeyer flask and incubated for 18 h at 55° C.

After cooling to room temperature the cells were harvested by centrifiugation at 10000 g for 8 min and the spent broth was filtered through a 0.22 μ membrane to remove the spores. Filtrate was concentrated by precipitating with 80% saturation of ammonium sulphate, dialysed and used as crude enzyme solution.

A strong fibrin-specific fibrinolytic enzyme was purified from the cell-free spent culture broth. The strain produced 150 mg crude protein l$^{-1}$ of spent broth, with a specific activity of 80 Plough units mg$^{-1}$, within 18 h of incubation at 55° C. in glucose yeast extract peptone medium, pH 8.0.

For production of the enzyme, the strain utilized different carbon and nitrogen sources with a C:N ratio of ~1:2. The enzyme was stable at a broad range of pH ranging from 5 to 9, and highly thermostable with 50% activity after storage 60° C. for 6 months. The enzyme belonged to the serine endopeptidase group. In vitro clot lysis revealed that the enzyme was active at 37° C.

Fibrinolytic Enzyme Assay

The fibrinolytic (thrombolytic) activity was assayed on solid and liquid media (Harverkate & Trass 1974, Lottenberg et al. 1981). The reaction mixture (1 ml) comprised of chromogenic substrates, such as benzoyl-β-alanyl-glycyl-arginine-ρnitroanilide (20 μ mol l$^{-1}$) in 10 mM sodium phosphate buffer, pH 8.0 and incubated at 55° C. for 30 min after addition of 1 ml, enzyme solution containing 0.5 μg protein ml$^{-1}$, cooled to room temperature and the liberation of ρ-nitroanilide was measured by increased absorbance recorded at 405 nm using a UV-VIS Spectrophotometer (DU 8B, Beckman, Sweden).

One unit of the enzyme was defined as the amount of enzyme that catalysed the formation of 1 ng of ρ-nitroanilide min$^{-1}$. The caseinolytic activity was determined by Dunn (1989) in terms of μmol tyrosine min$^{-1}$.

Protein was determined using Folin Ciocalteau phenol reagent. All the results of growth and assays are the means of three separate experiments.

Effect of pH and Temperature on Production of Fibrinolytic Enzyme

The optimum pH for enzyme production was determined at different pH values ranging from 5 to 9 using Citrate phosphate buffer, pH 5.0, Sodium phosphate buffer, pH 6.0–8.0 and Tris.HCl, pH 9.0–10.0. Stability to pH was determined by assaying the residual activity after exposure to different pH values ranging from 5.0 to 9.0.

Optimum temperature for production was determined by assaying the enzyme activity at different temperatures ranging from 35° C. to 70° C. for 18 h using GYP medium, pH 8.0.

Effect of Growth Period on the Production of the Enzyme by S. megasporus SD5

To determine the amount of the fibrinolytic and caseinolytic enzymes through out the growth period of 24 h, quantitation of the enzymes was carried out as mentioned above along with the growth, in terms of protein, at definite intervals.

Effect of Different Storage Times, at Different Temperatures Ranging from 35° C. to 70° C. on the Activity of the Enzyme Thermostability was determined by measuring the residual activities after storing the enzyme for 6 months at different temperatures ranging from 35° C. to 70° C. The enzyme solution in 10 mM phosphate buffer, pH 8.0 was stored at different temperatures (35° C. to 70° C.) for different periods (1–6 months) and the residual activity was determined at definite intervals, as mentioned previously and compared with the activity of the enzyme solution (as 100%) kept at 4° C. as control.

Effect of Different Carbon and Nitrogen Sources along with Inorganic Chemicals on the Production of the Enzyme by S. megasporus SD5.

The effects of different carbon and nitrogen sources as well as inorganic chemicals on the production of the enzyme were evaluated by supplementing the basal medium, pH 8.0 with different carbon and nitrogen sources followed by incubation at 55° C. for 18 h. The activities of the enzyme synthesized from different sources were compared with that of the control (GYP). Similarly the effects of different inorganic compounds on the synthesis of the enzyme were also determined.

Effects of Mutagenic Chemicals on the Synthesis of the Enzyme

To increase the synthesis of the enzyme, the spore suspension (0.6×10$^5$) of S. megasporus SD5 was exposed to different mutagenic substances, such as, N-methyl-N-nitro-N-nitrosoguanidine (NTG), ethyl methane sulphonate (EMS) and u.v. (254 nm) irradiation for different periods as in the standard protocol (Hopwood et al. 1985). The mutant colonies were inoculated in GYP for production of the enzyme and amount of the enzyme produced was marginal.

EXAMPLE 3

Production of the Fibrinolytic Enzyme Using *S. megasporus* SD5

Preparation of Seed Culture

After optimisation of the fibrinolytic enzyme at flask level, preparation of the seed culture was carried out. To prepare the seed culture, GYP medium, pH 8.0 (50 ml) containing 0.02% $CaCl_2$ was inoculated with 50 μl of spore suspension and incubated at 55° C. for 10 h and the resultant growth was used to inoculate 500 ml fresh pre-warmed (55° C.) GYP medium followed by incubation at 55° C. for 10 h.

Bench Scale Production of the Enzyme

In a laboratory scale (10 l) fermenter (MDL Marubishi, Japan) 5 l prewarmed medium (55° C.) was inoculated with 500 ml seed culture grown as mentioned earlier and incubation was continued for 18 h at 55° C. with agitation (150 rev min$^{-1}$) and aeration (400 ml min$^{-1}$). The fermented broth was cooled to room temperature and the density of the viable cells was determined. The cell mass was separated by centrifiugation at 10000 g for 10 min at 18° C. and the cell free spent broth was filtered through a 0.22-μm membrane to remove the spores. The protein was concentrated by precipitation with 80% saturation ammonium sulphate. The precipitate was dissolved in 100 ml of 10 mM phosphate buffer pH 8.0, dialysed against same buffer at ambient temperature for 12 h, freeze dried and used as crude enzyme preparation.

Gel Eletrophoresis

Post-eletrophoretic reactivity after non-denaturing PAGE was carried out according to Hames (1981) along with the standard proteins, in duplicate. One part was stained with Coomassie Blue R 250 and the other part was incubated with a fibrin plate for 2 h at 37° C. and the fibrinolytic activity was detected as a clear zone after staining the fibrin plate with Coomassie Blue.

To determine the class to which the enzyme belonged the effect of different protease inhibitors were studied in detail. As the fibrinolytic enzyme could be used as a therapeutic agent for different types of thrombosis so in vitro clot lysis was studied with both natural and synthetic clots.

EXAMPLE 4

Bacterial Strain and Culture Medium

*Streptomyces megasporus* SD5 was isolated from tectonic zone and identified to the cluster level. The medium used for culturing the strain consisted of (% w/v) glucose 1, yeast extract 0.5, peptone 0.5, NaCl 0.5 and $CaCl_2$ 0.2 with the pH being 8.0. The protein was collected from spent cell free broth after 18 hours of incubation at 55° C. and concentrated by ionic precipitation followed by purification using standard protocol. The yield of protein was 150 mg per liter of broth with a specific activity of 80 Umg$^{-1}$. In vitro study was carried out on the effects of actinokinase (0–100 μgml$^{-1}$) on the clotting time and the clot dissolution time using standard protocols.

The values obtained were compared with those of prior art enzymes. In vivo studies were carried out on rabbits after observing the immulogical responses of the wild and recombinant enzymes. The properties of the protein are given in Table X and the comparison of properties of the enzyme obtained with prior art enzymes is given in Table XI:

TABLE X

Characteristics of the protein actinokinase

| Properties | | Properties | |
| --- | --- | --- | --- |
| Class | Serine peptidase | Thermostability | 35° C.–70° C. |
| Clan | SA | Specific activity | 80 Umg$^{-1}$ |
| Family | S1 | Yield (crude) | 150 mgl$^{-1}$ |
| Mol Wt. | 35 kDA | Activity depends on | N-terminal |
| PI | 7.56 | Allergen | No |
| pH stability | 5–9 | haemolytic | No |

TABLE XI pharmacological properties of thrombolytic agents in acute myocardial infarctions

| Enzyme | Efficacy (<4h) | Dose | Relative cost | Adverse effects | Half life (mm) |
| --- | --- | --- | --- | --- | --- |
| Streptokinase | 65 | 1.5 MU | Low | Haemorragic | 23 |
| Staphylokinase | 30 | 10 mg | Low | Immunogenic | 60 |
| Urokinase | 65 | 2.5 MU | High | — | 16 |
| T-PA | 70 | 100 mg | High | — | 5 |
| APSAC | 65 | 30 mg | High | Haemorragic | 90 |
| Scu-PA | 70 | 50 mg | High | Immunogenic | 7 |
| Actinokinase | >80 | <5 mg | Very low | nil | >360 |

[T-PA, APSAC & Scu-PA data were taken from the literature}

EXAMPLE 5

The antigenicity, immunogenicity of actinokinase on rabbits and effects on blood cells and proteins Chemicals and Reagents The chemical required for Western blot using AP conjugate were obtained from Bio-Rad, Germany. Complete and Incomplete Freund's adjuvant was obtained from Genei, Bangalore, India. Acetonitrile, acetic acid, chloroform and ethanol of highest purity, along with disposable syringes and cotton, were purchased from the local market. Human fibrinogen, thrombin, streptoldnase, urokinase, plasminogen and plasmin, CAPS buffer and Ponceau S strain were purchased from Sigma (St. Louis, USA). Three rabbits belonging to New Zealand white species, 4 to 5 months old weighing 1.36, 1.45 kg and 1.5 Kg, were purchased from Serum Institute of India, Pune (Reg.No. 41/99/CPCSEA).

Immunization

All rabbits were acclimatized for 7 days in the laboratory premises and checked for weight, behaviour and body temperature (rectal). Blood was collected from the ear vein and processed to check the presence of natural antibody against the protein.

Preparation of the Antigens

The electrophoretically homogenous actinokinase was washed repeatedly with physiological saline under aseptic conditions and concentration was adjusted to 100 μg ml$^{-1}$. The purity of the protein, detected by HPLC at 220 nm using a Lichrosphere 100 RP-18 encapped (5 μm) in LichroCART (Merck) column and 10 mM phosphate buffer, pH 7.2 as solvent system.

Antisera were raised in rabbits using standard protocol (Blake et al 1984). Protein solution (100 μg ml$^{-1}$) along with 1 ml Freund's complete adjuvant was injected subcutaneously in the subscapular region of rabbits. The body temperature, food habits and behaviour pattern were observed continuously through out the experiment. After 10 days 10 ml blood was collected and processed for preparation of antisera and 100 μg protein along with I ml Freund's incomplete adjuvant was injected. After 10 days the rabbits were given booster dose of only 100 kg protein and more blood was collected within 7 days.

For immunological studies 3 types of analysis was carried out: a) Classical precipitin test (Roitt 1988), b) Ouchterlony double diffusion test (Ouchterlony 1987) and c) Immuno blotting (Towbin and Gordon 1984) using AP-conjugate (Rastichian 1992) and Western Processor (Bio-Rad). The antigens were electrophoresed in SDS-polyacrylamide gels followed by Immunoblotting. Western blots (Yamamoto et al 2000) were carried out using pure actinokinase.

In Vivo and in Vitro Clot Lysis

A preliminary experiment was carried out to determine in vivo clot lysis. 250 μg protein in 10 mM PBS was injected in the ear, full of clot, of a rabbit and disappearance of the haematoma was observed continuously along with behavioral changes. In vitro clot lysis assay was carried out using dropping glass bead type experiment as per Plough and Kjeldgaard (1957) and synthetic clot prepared with plasma, CaCl$_2$ and NaCl and the activity was determined using standard urokinase, obtained from National Institute of Biological Standard and Controls, Hertfordshire, UK under the guidance of World Health Organization.

Hemolytic Effect

To determine the effect of actinokinase on blood cells, 2 ml diluted blood cells was incubated with 500 μl (50 μg) actinokinase at 37° C. for 30 min along with control containing clot and buffer. The cell morphology was compared with those of the control using a phase contrast microscope (Nikon, Japan). Lytic effect of actinokinase was also checked on plate (Kim at al 1997) using both positive and negative controls. All experiments were carried out in triplicate.

Results

During acclimatization the animals were normal and natural antibodies against actinokinase was absent. The rabbits were healthy after the final shots and neither behavior nor temperature change were noted even after final dose. The rabbits actually gained weight ranging from 400–500 gm within 30 days indicating that actinokinase was non toxic to animals. This was further proved by acute toxicity tests. Quantitative precipitin reaction between actinokinase and anti-actinokinase showed that Zone of equivalence seemed to be at 0.6–0.8 ug of antigen. With Ouchterlony double diffusion test a single precipitin line was observed after 18 h after the addition of antisera which might indicate that this antigen-antibody complex was a single component system. The formation of a single band in precipitin reaction, Ouchterlony test and in immunoelectrophoresis confirmed single number of reacting components and the immunological relationship between wild and recombinant antigens (Maruyama and Nakajima 1993). The width of the line was increased with the doses, being minimum with first dose and maximum with the last dose. This might signify the increased production of anti body or might be due to a polycomponent system. The immuno-blotting of actinokinase produced a single band corresponding with a 35 kDa-protein band in SDS-Page of actinokinase, which revealed the purity of the antigen and with a single component system (Nakajima et al 1993).

In vivo clot lysis revealed that within 30 min 50% of the clotted region became clear. Though in this experiment, the concentration of actinokinase/metabolites effect of as actinokinase or excretion pattern could not be traced but from biochemical test it was observed that the protein was quite stable at 37° C. In vitro lytic effect of actinokilase on clots with oxalated plasma and with fibrinogen within 20–30 min at 37° C.

The microscopic studies of blood cells, before and after enzyme treatment revealed no deformity or lysis of the red blood cells Clear cell out line like control was observed in the experimental also (FIG. 3). This was further clear on the blood agar plate with a positive control Arthrobactor sp. and negative control, urokinase even after overnight incubation at 37° C. (FIG. 4). The proteolytic activity on thrombin, hemoglobin, bovine serum albumin and fibrinogen was given in Table XII, which proved that though actinokinase exhibited fibrinolytic activity but it was not harmful to blood cells or proteins

TABLE XII

Relative proteolytic activity of actinokinase on blood proteins

| Substrate | Relative activity (%) |
|---|---|
| Fibrin | 100 |
| Thrombin | 27 |
| Hemoglobin | 8 |
| Fibrinogen | 12 |
| Bovine serum albumin | 32 |

This proved the superiority of actinokinase as a therapeutic agent when compared with streptokinase or staphylokinase (Rao et al 1988)

Advantages of the Invention

1. Prior art fibrinolytic enzymes obtained from prokaryotes are not hydrolase—they bind with inactive plasminogen to change it to active plasmin as a bound form. The enzyme of the invention on the other hand, being a eukaryotic protein, hydrolyses the fibrin threads and thereafter becomes free to react again.
2. The production time and purification cost are low, thereby reducing the cost of producing the units of the enzyme and thereby reducing the cost of the product.
3. The shelf life of the product is high when compared with prior art enzymes.
4. There are no side effects in the use of the enzyme of the invention.

We claim:

1. An enzyme extracted and isolated from the microorganism *Streptomyces megasporus* SD5 or mutant thereof which is isolated by a process which comprises the steps of:
   a) cultivating the microorganism *Streptomyces megasporus* SD5 or mutant thereof under aerobic conditions at a temperature in the range of 45° C. to 65° C. in an alkaline aqueous nutrient medium and
   b) recovering the enzyme.

2. A process for isolating an enzyme from the microorganism *Streptomyces megasporus* SD5 comprising cultivating the microorganism *Streptomyces megasporus* SD5 or mutant thereof under aerobic conditions at a temperature in the range of 45° C. to 65° C. in an alkaline aqueous nutrient medium and recovering the enzyme.

3. The process as claimed in claim 2 wherein the nutrient medium comprises carbon sources, nitrogen sources, salts and trace elements and is at a pH of 7.5 to 9.0.

4. The process as claimed in claim 3 wherein the carbon source is selected from the group consisting of glucose, soluble starch and raw starch.

5. The process as claimed in claim 3 wherein the nitrogen source is selected from the group consisting of yeast extract, peptone, tryptone, casein and casein hydrolysate.

6. The process as claimed in claim 3 wherein the salts used are selected from the group consisting of chlorides of calcium, sodium, potassium and magnesium.

7. The process as claimed in claim 3 wherein the trace elements are selected from the group consisting of iron, manganese, copper, zinc, borate and molybdenum.

8. The process as claimed in claim 3 wherein the temperature is maintained in the range of 50° C.–55° C. and the cultivation is carried out by fermentation.

9. The process as claimed in claim 8 wherein an anti-foam agent is added to the nutrient medium during fermentation.

10. The process as claimed in claim 8 wherein the enzyme is concentrated with ammonium sulphate and then separated from other proteins.

11. The process as claimed in claim 10 wherein the concentrated enzyme is separated by gel filtration, ion exchange chromatography and isoelectric focusing in the presence of a buffer having a pH in the range of 3–10.

12. A method for the treatment of thrombolytic disorders comprising administering a pharmaceutically acceptable dosage of enzyme of claim 1.

13. An enzyme extracted and isolated from the microorganism *Streptomyces megasporous* SD5 which is a serine protease of 264 amino acids and has a molecular weight of about 35 kDa as determined by SDS-PAGE.

14. The enzyme according to claim 1 which is a serine protease of 264 amino acids and has a molecular weight of about 35 kDa as determined by SDS-PAGE.

15. The enzyme according to claim 13 wherein the amino acid composition per 100 residues is:

| | | | |
|---|---|---|---|
| Asp | 3.7 | Val | 9.0 |
| Glu | 4.1 | Pro | 14.1 |
| Asn | 3.1 | Trp | 10.5 |
| Glu | 3.1 | Phe | 2.9 |
| Ser | 6.2 | Ile | 1.4 |
| Thr | 5.1 | Leu | 7.2 |
| Gly | 3.8 | Arg | 2.8 |
| Ala | 10.7 | His | 9.3 |
| Tyr | 3.0 | | |

16. The enzyme according to claim 14 wherein the amino acid composition per 100 residues is:

| | | | |
|---|---|---|---|
| Asp | 3.7 | Val | 9.0 |
| Glu | 4.1 | Pro | 14.1 |
| Asn | 3.1 | Trp | 10.5 |
| Glu | 3.1 | Phe | 2.9 |
| Ser | 6.2 | Ile | 1.4 |
| Thr | 5.1 | Leu | 7.2 |
| Gly | 3.8 | Arg | 2.8 |
| Ala | 10.7 | His | 9.3 |
| Tyr | 3.0 | | |

17. The enzyme according to claim 15 wherein the N-terminal amino acid sequence of the first 16 residues is D-E-N-Q-S-T-G-A-Y-V-P-P-Y-F-I-L.

18. The enzyme according to claim 16 wherein the N-terminal amino acid sequence of the first 16 residues is D-E-N-Q-S-T-G-A-Y-V-P-P-Y-F-I-L.

19. The enzyme according to claim 14 wherein the enzyme has optiminum activity at a pH of 7 to 8.5.

20. The enzyme according to claim 14 wherein the enzyme has a pI of 7.56.

21. The enzyme according to claim 14 wherein the enzyme is stable in a pH range of from 5 to 9.

22. The enzyme according to claim 14 wherein the enzyme is active at 37° C.

23. The process according to claim 2 wherein the enzyme extracted from the microorganism *Streptomyces megasporous* SD5 is a serine protease of 264 amino acids and has a molecular weight of about 35 kDa as determined by SDS-PAGE.

24. The process according to claim 23 wherein the amino acid composition per 100 residues of the enzyme is:

| | | | |
|---|---|---|---|
| Asp | 3.7 | Val | 9.0 |
| Glu | 4.1 | Pro | 14.1 |
| Asn | 3.1 | Trp | 10.5 |
| Glu | 3.1 | Phe | 2.9 |
| Ser | 6.2 | Ile | 1.4 |
| Thr | 5.1 | Leu | 7.2 |
| Gly | 3.8 | Arg | 2.8 |
| Ala | 10.7 | His | 9.3 |
| Tyr | 3.0 | | |

25. The process enzyme according to claim 24 wherein the N-terminal amino acid sequence of the first 16 residues of the enzyme is D-E-N-Q-S-T-G-A-Y-V-P-P-Y-F-I-L.

26. The process as claimed in claim 18 wherein the fermentation is submerged fermentation.

27. The process as claimed in claim 9 wherein the anti-foam agent is soybean oil.

28. The enzyme according to claim 1 wherein in the process for isolating the enzyme the nutrient medium comprises carbon sources, nitrogen sources, salts and trace elements and is at a pH of 7.5 to 9.0.

29. The enzyme according to claim 28 wherein the carbon source used in the isolation of the enzyme is selected from the group consisting of glucose, soluble starch and raw starch.

30. The enzyme according to claim 28 wherein the nitrogen source used in the isolation of the enzyme is selected from the group consisting of yeast extract, peptone, tryptone, casein and casein hydrolysate.

31. The enzyme according to claims 28 wherein the salts used in the isolation of the enzyme are selected from the group consisting of chlorides of calcium, sodium, potassium and magnesium.

32. The enzyme according to claim 28 wherein the trace elements used in the isolation of the enzyme are selected from the group consisting of iron, manganese, copper, zine, borate and molybdenum.

33. The enzyme according to claim 28 wherein in the process for isolating the enzyme the temperature is maintained in the range of 50° C.–55° C. and the cultivation is carried out by fermentation.

34. The enzyme according to claim 33 wherein in the process for isolating the enzyme the enzyme is concentrated with ammonium sulphate and then separated from other proteins.

35. The enzyme according to claim 34 wherein the concentrated enzyme is separated by gel filtration, ion exchange chromatography and isoelectric focusing in the presence of a buffer having a pH in the range of 3–10.

36. An enzyme extracted from the microorganism *Streptomyces megasporous* SD5 prepared by the process which comprises the steps of:
  a) cultivating the microorganism *Streptomyces megasporus* SD5 under aerobic conditions at a temperature in the range of 45° C. to 65° C. in an alkaline aqueous nutrient medium and
  b) recovering the enzyme.

* * * * *